(12) United States Patent
Newell

(10) Patent No.: US 10,041,096 B2
(45) Date of Patent: Aug. 7, 2018

(54) METHODS AND PRODUCTS FOR GENERATING OILS

(71) Applicants: The Texas A&M University System, College Station, TX (US); Scott & White Healthcare, Temple, TX (US)

(72) Inventor: Martha Karen Newell, Holland, TX (US)

(*) Notice: Subject to any disclaimer, the term of this patent is extended or adjusted under 35 U.S.C. 154(b) by 805 days.

(21) Appl. No.: 14/357,679

(22) PCT Filed: Nov. 9, 2012

(86) PCT No.: PCT/US2012/064334
§ 371 (c)(1),
(2) Date: Nov. 12, 2014

(87) PCT Pub. No.: WO2013/071029
PCT Pub. Date: May 16, 2013

(65) Prior Publication Data
US 2015/0111263 A1  Apr. 23, 2015

Related U.S. Application Data

(60) Provisional application No. 61/558,727, filed on Nov. 11, 2011.

(51) Int. Cl.
| | | |
|---|---|---|
| *C12P 7/64* | (2006.01) | |
| *C12N 1/12* | (2006.01) | |
| *C12N 1/14* | (2006.01) | |
| *C12N 1/38* | (2006.01) | |
| *C07C 67/02* | (2006.01) | |
| *C10L 1/02* | (2006.01) | |
| *C10L 1/08* | (2006.01) | |
| *C10L 3/00* | (2006.01) | |

(52) U.S. Cl.
CPC ............ *C12P 7/6463* (2013.01); *C07C 67/02* (2013.01); *C10L 1/026* (2013.01); *C10L 1/08* (2013.01); *C10L 3/00* (2013.01); *C12N 1/12* (2013.01); *C12N 1/14* (2013.01); *C12N 1/38* (2013.01); *C10L 2200/0476* (2013.01); *C10L 2200/0492* (2013.01); *C10L 2270/026* (2013.01); *C10L 2290/02* (2013.01); *C10L 2290/42* (2013.01); *Y02E 50/13* (2013.01)

(58) Field of Classification Search
CPC ....................................................... C12N 1/12
See application file for complete search history.

(56) References Cited

U.S. PATENT DOCUMENTS

| | | | |
|---|---|---|---|
| 2011/0078946 A1* | 4/2011 | Newell | C10L 1/026 44/388 |
| 2012/0178123 A1* | 7/2012 | Rosen | C12M 21/02 435/42 |

OTHER PUBLICATIONS

Cohen et al., Overproduction of gamma-linolenic and Eicosapentaenoic acids by Algae, Plant PHysiology, 1992, vol. 98, p. 569-572.*

* cited by examiner

*Primary Examiner* — Taeyoon Kim
*Assistant Examiner* — Tiffany M Gough
(74) *Attorney, Agent, or Firm* — Berliner & Associates

(57) ABSTRACT

Compositions and methods for enhancing secretion of oils from oil producing cells are described herein. In particular, secretion of oils is enhanced by treating the cells with herbicides. The oils generated according to the invention may be useful, for example, in the production of biofuels.

12 Claims, 14 Drawing Sheets

Culture cell densities over the course of the study.

Lipids detected in total extracts from the sodium oxamate study

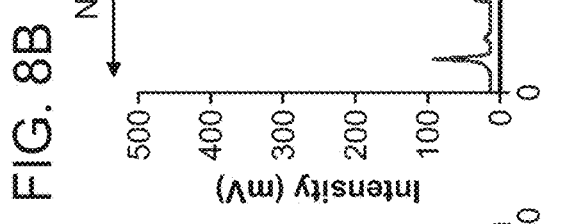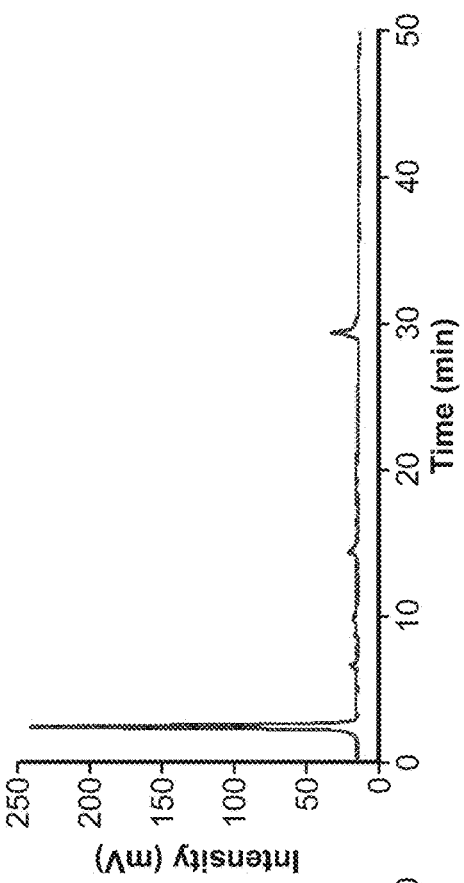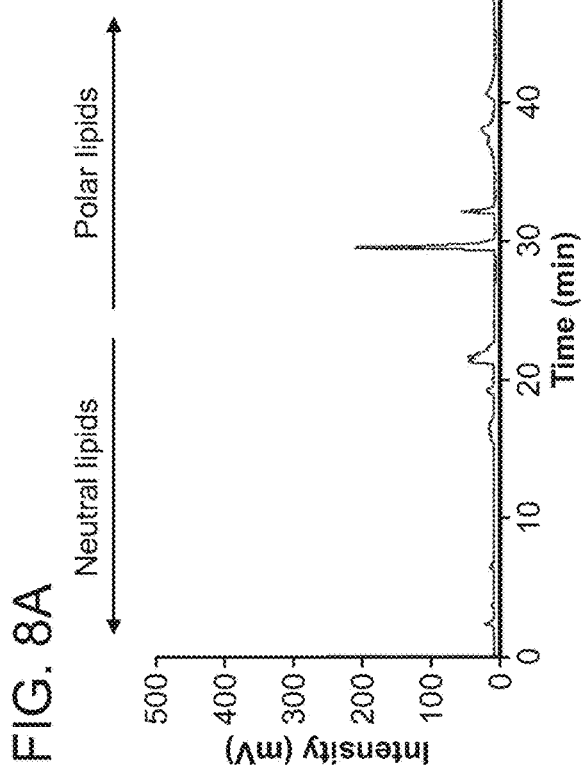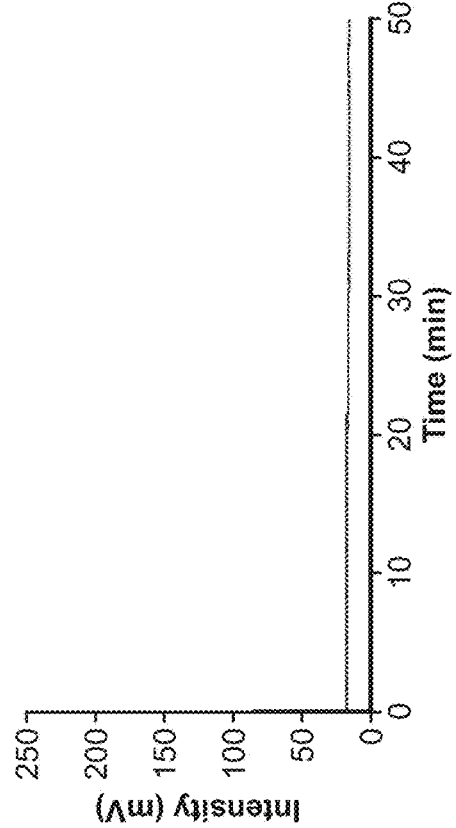

SEQUENCE LISTING

```
<160> NUMBER OF SEQ ID NOS: 2

<210> SEQ ID NO 1
<211> LENGTH: 362
<212> TYPE: DNA
<213> ORGANISM: Homo sapiens
<220> FEATURE:
<221> NAME/KEY: 2,4-dienoyl-CoA reductase
<222> LOCATION: (1)..(362)

<400> SEQUENCE: 1
```

-continued

```
taagctttaa aaacatgtaa aaaggacatt aaattgacat cttttttgtg ttaggtcacc      60
aaggagcagt gggacaccat agaagaactc atcaggaaga caaaaggttc ctaagaccac     120
tttggccttc atcttggtta cagaaaaggg aatagaaatg aaacaaatta tctctcatct     180
tttgactatt tcaagtctaa taaattctta attaacaaac attcattgaa tatgtattat     240
gtgccaggcc agtgatagcc attgtatatt caaagataaa taaatgaaa tatagtcttc     300 aaaacattaa aaaaaaagg agggcatggg gagagtaggt aaaggctcct ctttacctat     360
tt                                                                    362
```

<210> SEQ ID NO 2
<211> LENGTH: 334
<212> TYPE: PRT
<213> ORGANISM: Homo sapiens
<220> FEATURE:
<221> NAME/KEY: 2,4-dienoyl-CoA reductase
<222> LOCATION: (1)..(334)

<400> SEQUENCE: 2

```
Met Lys Leu Pro Ala Arg Val Phe Phe Thr Leu Gly Ser Arg Leu Pro
1               5                   10                  15

Cys Gly Leu Ala Pro Arg Arg Phe Phe Ser Tyr Gly Thr Lys Ile Leu
            20                  25                  30

Tyr Gln Asn Thr Glu Ala Leu Gln Ser Lys Phe Phe Ser Pro Leu Gln
        35                  40                  45

Lys Ala Met Leu Pro Pro Asn Ser Phe Gln Gly Lys Val Ala Phe Ile
    50                  55                  60

Thr Gly Gly Gly Thr Gly Leu Gly Lys Gly Met Thr Thr Leu Leu Ser
65                  70                  75                  80

Ser Leu Gly Ala Gln Cys Val Ile Ala Ser Arg Lys Met Asp Val Leu
                85                  90                  95

Lys Ala Thr Ala Glu Gln Ile Ser Ser Gln Thr Gly Asn Lys Val His
            100                 105                 110

Ala Ile Gln Cys Asp Val Arg Asp Pro Asp Met Val Gln Asn Thr Val
        115                 120                 125

Ser Glu Leu Ile Lys Val Ala Gly His Pro Asn Ile Val Ile Asn Asn
    130                 135                 140

Ala Ala Gly Asn Phe Ile Ser Pro Thr Glu Arg Leu Ser Pro Asn Ala
145                 150                 155                 160

Trp Lys Thr Ile Thr Asp Ile Val Leu Asn Gly Thr Ala Phe Val Thr
                165                 170                 175

Leu Glu Ile Gly Lys Gln Leu Ile Lys Ala Gln Lys Gly Ala Ala Phe
            180                 185                 190

Leu Ser Ile Thr Thr Ile Tyr Ala Glu Thr Gly Ser Gly Phe Val Val
        195                 200                 205

Pro Ser Ala Ser Ala Lys Ala Gly Val Glu Ala Met Ser Lys Ser Leu
    210                 215                 220

Ala Ala Glu Trp Gly Lys Tyr Gly Met Arg Phe Asn Val Ile Gln Pro
225                 230                 235                 240

Gly Pro Ile Lys Thr Lys Gly Ala Phe Ser Arg Leu Asp Pro Thr Gly
                245                 250                 255

Thr Phe Glu Lys Glu Met Ile Gly Arg Ile Pro Cys Gly Arg Leu Gly
            260                 265                 270

Thr Val Glu Glu Leu Ala Asn Leu Ala Ala Phe Leu Cys Ser Asp Tyr
        275                 280                 285
```

```
Ala Ser Trp Ile Asn Gly Ala Val Ile Lys Phe Asp Gly Gly Glu Glu
    290                 295                 300

Val Leu Ile Ser Gly Glu Phe Asn Asp Leu Arg Lys Val Thr Lys Glu
305                 310                 315                 320

Gln Trp Asp Thr Ile Glu Glu Leu Ile Arg Lys Thr Lys Gly
                325                 330
```

METHODS AND PRODUCTS FOR GENERATING OILS

RELATED APPLICATIONS

This application claims priority under 35 U.S.C. § 119(e) to U.S. Provisional Application Ser. No. 61/558,727, entitled "METHODS AND PRODUCTS FOR GENERATING OILS" filed on Nov. 11, 2011, which is herein incorporated by reference in its entirety.

FIELD OF THE INVENTION

The present invention relates to compositions and methods for enhancing secretion of oils from oil producing cells. In particular, secretion of oils is enhanced by treating the cells with herbicides. The oils generated according to the invention may be useful, for example, in the production of biofuels.

BACKGROUND OF THE INVENTION

Long term energy solutions to global energy challenges increasingly include renewable fuels. Renewable energy sources include electric, solar, wind and biofuels. Only biofuels have the potential to act as feedstock for existing refineries and the resulting biofuel will have similar molecular structure to the refined petroleum products currently used for transportation fuel. Current refineries have the capability for hydrogenation and hydrocracking to further refine the fatty acids into usable transportation fuels. Advanced refining reduces the possibility of gelling in lower temperatures which is a criticism of biofuels. Leading biofuel sources include corn, sugar cane, palm, soy and algae. Algae has the potential to produce impressive increases in gallons/acre of oil production compared to other biofuel sources. Some report yields up to 100 times greater (Tachibana, C. (2009). Algae Biofuels: From pond Scum to Jet Fuel (Oregon, United States, RenewableEnergyWorld.com), pp. 2.). Unlike agricultural sources for biofuel which require extensive land allotments that compete with natural forests and habitats and compete with food production imparting upward pressure on world food prices, algae-based biofuel can be grown in areas unfavorable for traditional agriculture.

SUMMARY OF THE INVENTION

The invention in some aspects relates to the discovery that herbicides are useful for enhancing oil secretion from oil producing cells. In one aspect, the invention is a method involving contacting an oil producing cell with an herbicide in an effective amount to promote secretion of oil by the cell and collecting the oil from the oil producing cell.

The herbicide in some embodiments is a sulfonylurea. Sulfonylureas include but are not limited to Chlorpropamide (Diabinese®), glimepiride (Amaryl®), glyburide (Micronase®, Diabeta®), glipizide (Glucotrol®), Tolazamide (Tolinase®), and Tolbutamide (Orinase®). In some embodiments the sulfonylurea is glyburide.

In some embodiments the method is a method for preparing a biofuel and further comprises processing the oil to produce a biofuel. The methods can involve any art known methods for preparing a biofuel. In some embodiments the oil is processed to produce biofuel using a thermochemical liquification process. In other embodiments the oil is processed to produce biofuel using a pyrolysis process. In other embodiments the oil may be processed for other purposes such as food or food supplements.

The oil producing cell may be a plant or a fungus, such as an algae. In some embodiments the algae is a *schizochytrium*.

The biofuel may be a syngas. Syngas may be processed, for instance, by a Fischer-Tropsch reaction to produce a biodiesel. Alternatively the biofuel may be biodiesel. In some embodiments the biodiesel is processed using a transesterification process, for example, such as that which is achieved by mixing the oil with methanol.

The method involves, in other embodiments, contacting the oil producing cell with an inhibitor of fatty acid metabolism. In some embodiments the oil producing cells are treated with the inhibitor of fatty acid metabolism prior to being treated with the herbicide. For example, the oil producing cells may be treated with the inhibitor of fatty acid metabolism at least 24 hours before being treated with the herbicide or 24-96 hours before being treated with the herbicide or about 48 hours before being treated with the herbicide.

In some embodiments the fatty acid metabolism inhibitor is an inhibitor of fatty acid oxidation, a fatty acid transporter inhibitor, a reductase inhibitor, or an isomerase inhibitor within the fatty acid metabolism pathway.

The inhibitor of fatty acid metabolism may be an inhibitory nucleic acid. The inhibitory nucleic acid may be, for instance, specific for an enzyme selected from the group consisting of 2,4-dienoyl-CoA reductase, 2,4-dienoyl-CoA isomerase, and butyryl dehydrogenase. In some embodiments the algae or other oil producing cell may be a cell which has been engineered to constitutively or inducibly express an inhibitory nucleic acid or other fatty acid metabolism inhibitor.

In other embodiments the inhibitor of fatty acid metabolism is oxamate. The oxamate may be, for instance an alkyl oxamate such as, ethyl oxamate or sodium oxamate.

In yet another embodiment, the inhibitor of fatty acid metabolism is a compound having the following structure:

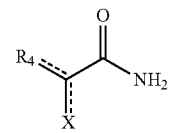

or a pharmaceutically acceptable salt or prodrug thereof, wherein $R_4$ is defined herein; wherein the dashed line is a double bond at one of the indicated positions and a single bond in the other; wherein $R_4$ is $O-C-CH_3$, $-ONa$, $-OH$, $-O-(CH_2)_3-CH_3$, $-CH_2-C(O)-C(O)-O-R_8$ or $-CH=C(OH)-C(O)-O-R_8$, alkyl, cycloalkyl, aryl, aralkyl, heteroaryl, heteroaralkyl, heterocyclyl, heterocycloalkyl, substituted alkyl, substituted cycloalkyl or substituted aryl, substituted aralkyl, substituted heteroaryl, substituted heteroaralkyl, substituted heterocyclyl, substituted heterocycloalkyl; wherein X is: $=O$, $=N-OR_2$; and wherein $R_2$ is independently selected from hydrogen, $H_2$, alkyl, cycloalkyl, aryl, substituted alkyl, substituted cycloalkyl or substituted aryl.

The method involves the use of a fatty acid metabolism inhibitor that is an oxirane carboxylic acid compound capable of inhibiting fatty acid metabolism, or a pharmacologically acceptable salt thereof in some embodiments.

In some embodiments the oxirane carboxylic acid compound has the formula:

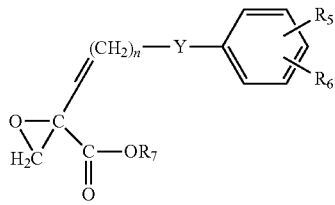

or a pharmaceutically acceptable salt or prodrug thereof, wherein $R_5$, $R_6$ and $R_7$ are herein; wherein $R_5$ represents a hydrogen atom, a halogen atom, a 1-4C alkyl group, a 1-4C alkoxy group, a nitro group or a trifluoromethyl group, $R_6$ has one of the meanings of $R_5$, $R_7$ represents a hydrogen atom or a 1-4C alkyl group, Y represents the grouping —O—$(CH_2)_m$—, m is 0 or a whole number from 1 to 4, and n is a whole number from 2 to 8 wherein the sum of m and n is a whole number from 2 to 8. $R_5$ in some embodiments is a halogen atom, $R_6$ is a hydrogen atom, m is 0, and n is 6. In other embodiments $R_7$ is an ethyl group. The oxirane carboxylic acid compound is etomoxir in some embodiments.

The methods may also involve the use of a glycolytic inhibitor. Glycolytic inhibitors include, for instance, a 2-deoxyglucose compound, such as 2-deoxyglucose compounds having the formula:

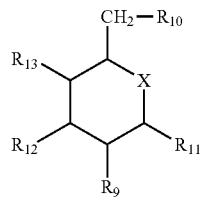

or a pharmaceutically acceptable salt or prodrug thereof, wherein $R_9$, $R_{10}$, $R_{11}$, $R_{12}$, and $R_{13}$ are herein; wherein X represents an O or S atom; $R_9$ represents a hydrogen atom or a halogen atom; $R_{10}$ represents a hydroxyl group, a halogen atom, a thiol group, or CO—$R_6$; $R_{11}$, $R_{12}$, and $R_{13}$ each represent a hydroxyl group, a halogen atom, or CO—$R_{14}$, $R_{14}$ represents an alkyl group of from 1 to 20 carbon atoms, and at least two of $R_{11}$, $R_{12}$, and $R_{13}$ are hydroxyl groups. In one embodiment the 2-deoxyglucose compound is 2-deoxy-D-glucose.

In yet other embodiments the oil producing cell is genetically modified for enhanced oil production.

A syngas composed of a gaseous mixture of hydrogen and carbon monoxide produced from an oil producing cell contacted with a sulfonylurea is provided in other aspects of the invention.

A biodiesel composed of a liquid diesel fuel produced from an oil producing cell contacted with a sulfonylurea is provided according to yet other aspects of the invention.

In other aspects the invention is an oil comprising a mixture of at least 90% hydrocarbon and lipids of intermediate polarity wherein the oil mixture is substantially free of β-carotene and chlorophyll.

In other aspects the invention is a method involving contacting an oil producing cell with an herbicide in an effective amount to promote secretion from the cells of recoverable oil in excess of 1 mg/L accumulated.

In other aspects the invention is a method for reducing toxin secretion in an algae, by contacting an algae with a fatty acid metabolism inhibitor in an effective amount to reduce toxin production. The methods further comprise testing culture liquid of the algae for toxins in some embodiments. In other embodiments the algae are treated with a compound for enhancing oil production and wherein the compound is not a fatty acid metabolism inhibitor. In yet other embodiments the algae is treated with the fatty acid metabolism inhibitor in a single dose.

Each of the limitations of the invention can encompass various embodiments of the invention. It is, therefore, anticipated that each of the limitations of the invention involving any one element or combinations of elements can be included in each aspect of the invention.

BRIEF DESCRIPTION OF THE DRAWINGS

FIG. 8 is a set of representative chromatograms from untreated controls, oxamate-, and glyburide-treated samples from the same *Chlorella* (algae) culture. 8A) shows untreated control at time=0, 8B) shows sodium oxamate-treated (0.3 mM) at 48 h, 8C) shows extracellular lipid profile from the untreated control (same culture as shown for the glyburide traces), 8D) shows extracellular lipid profile from the glyburide-treated (0.05 mM) at 24 h. Neutral lipids were eluted from the column within 24 min, while polar lipids elute with retention times >24 min.

DETAILED DESCRIPTION

Figure 1:
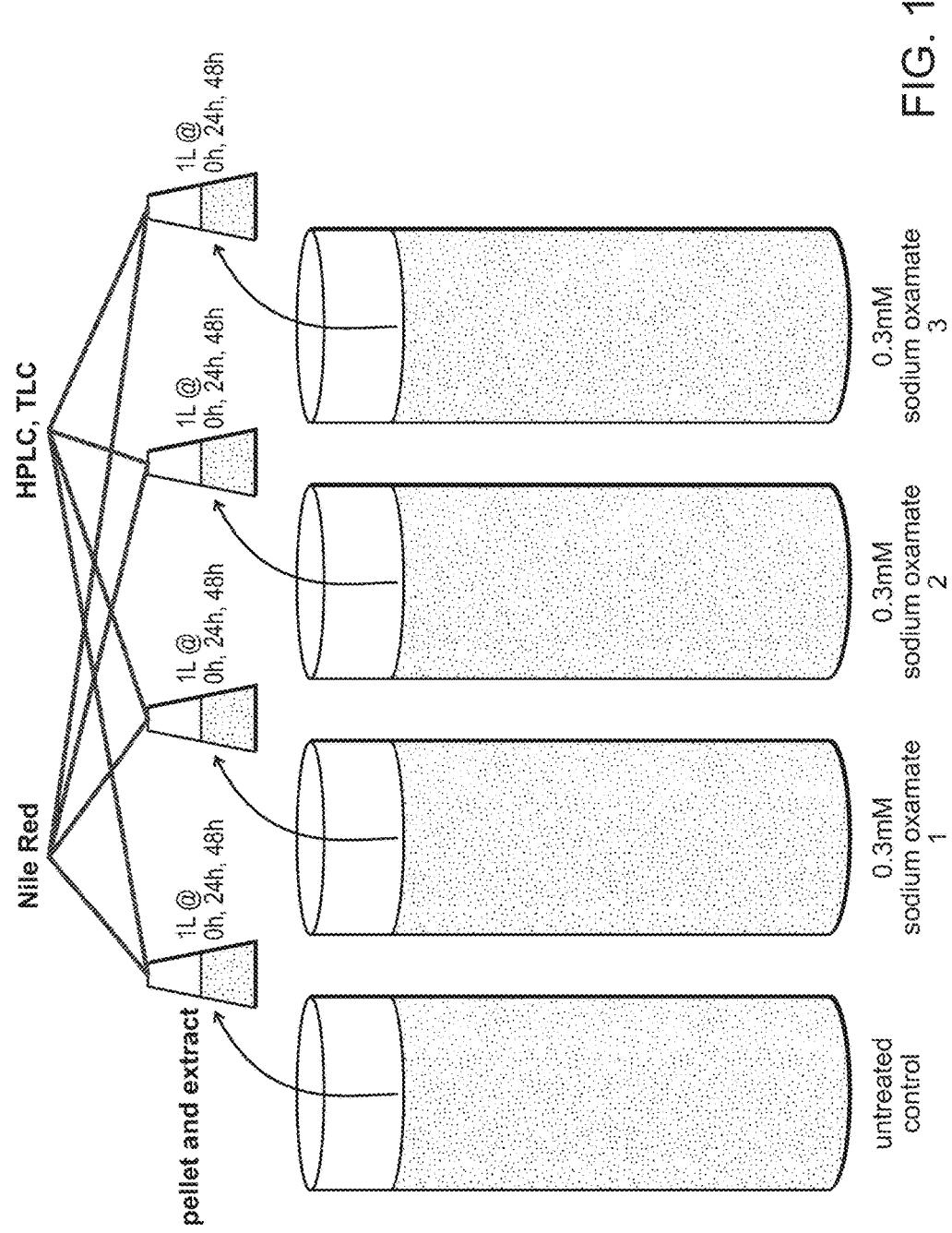
FIG. 1 is a schematic diagram of an experimental approach for sodium oxamate treatment of algae.

It has been discovered according to the invention that the processing and secretion of fatty acids in oil producing cells such as plants, including algae and types of fungi which are algae-like, and seeds, can be manipulated in a manner that results in the enhanced secretion of significant amounts of lipids/oils (fatty acids). These oils are useful for a number of purposes. For instance, they can be converted to biofuels.

New methods for enhancing oil accumulation and promoting the externalization of oil from live cells are described herein. By enhancing oil content metabolically, rather than manipulating growth conditions, and promoting the secretion or release of oil from cells without causing cell death or having to destroy the cells, the methods described herein may markedly reduce the cost and/or time of oil feedstock production from oil producing cells.

The data presented herein demonstrate the efficacy of the claimed method in research size batches as well as large commercial size growth volumes. The oil accumulation and excretion in the larger study are consistent with smaller scale results, further demonstrating the scalability of the methods. Quite surprisingly, greater than 1 mg/L quantities of oil were secreted from the cells in the treated large batch cultures. These results demonstrate that useful quantities of oil can be obtained using these methods. As shown in the Examples, algae such as *P. parvum* respond well to both oxamate (not only in producing more lipids, but also in growing faster to higher cell concentrations in small-scale culture) and to glyburide.

The methods of the invention utilize a class of compounds that have previously been identified as herbicides in order to enhance secretion of the oil from the oil producing cells. As shown in the examples, treatment of algae with an herbicide causes release of oil from the algae without apparently slowing the growth of the algae or causing cell death. In prior art systems for generating oil from algae, the algae need to be treated such that the oil can be removed from the algae. One advantage of the instant invention is that the oil released from algae can be captured and the algae can be left to continue to produce more oil. The methods of the invention resulted in an average of 1.4 mg/L total lipid recovered outside the cells at 24 hours (compared to 0.2 mg/L in controls). The total amount of hydrocarbon detected also trended higher in the treated groups.

The methods of the invention are achieved by treating an oil producing cell with an herbicide. Treatment of oil producing cells with an herbicide, as shown in the Examples, causes production of an oil sheen on the surface of the media, demonstrating that oil was released from cells. An herbicide, as used herein, is defined as a compound that is used to kill unwanted plants. The herbicides of the invention are those that inhibit high-affinity ATP-sensitive potassium ($K_{ATP}$) channel receptors at the plasma membrane of the oil producing cells. Thus, the herbicides of the invention are $K_{ATP}$ channel receptor inhibitors. These herbicides include but are not limited to sulfonylureas, PNU-37883A (a guanidine described in Meisheri et al., 1993a), PNU-89692, PNU-97025E and PNU-99963 (each described in Khan et al JPET Dec. 1, 1997 vol. 283 no. 3 1207-1213), HMR 1098, diazoxide, and pinacidil, (described in Gonca et al J CARDIOVASC PHARMACOL THER December 2010 vol. 15 no. 4 403-411).

Sulfonylureas bind to the ATP-dependent K+($K_{ATP}$) channel on the cell membrane and block channel activity. Sulfonylureas have the following basis structure.

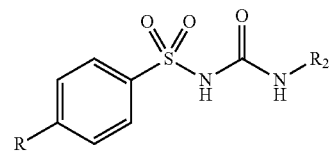

Sulfonylureas include but are not limited to Carbutamide, Acetohexamide, Chlorpropamide, Tolbutamide, Tolazamide, Glipizide, Gliclazide, Glibenclamide (glyburide), Gliquidone, Glyclopyramide, and Glimepiride. Other sulfonylureas can be identified by the skilled artisan based on the structures provide herein and others that are well known in the art, and are useful in the invention.

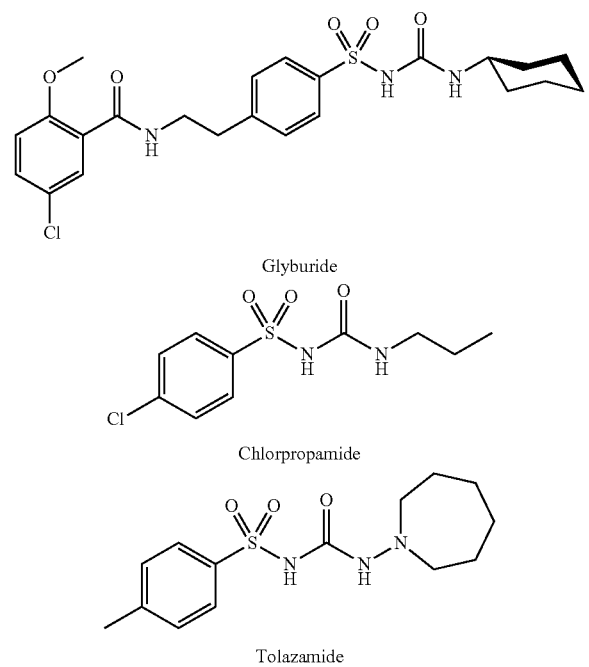

Glyburide

Chlorpropamide

Tolazamide

-continued

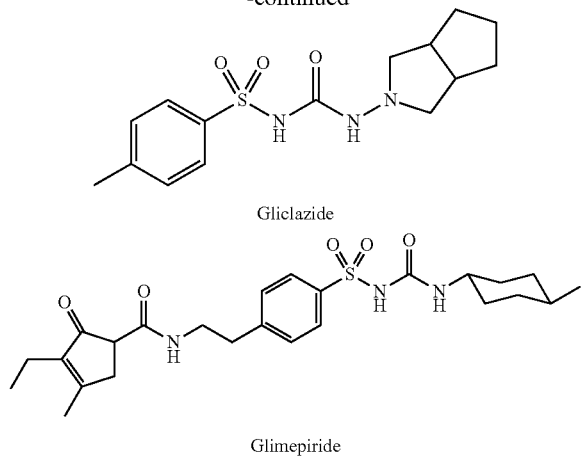

Gliclazide

Glimepiride

The methods described herein are useful in oil producing cells. An oil producing cell, as used herein is any cell that produces an oil (also referred to herein, interchangeably, as a lipid or fatty acid) which can be harvested. Typically oil producing cells of the invention are plant cells or fungi. As used herein, the term "plant" is used in its broadest sense. The term plant includes, but is not limited to, any species of woody, ornamental or decorative, crop or cereal, fruit or vegetable plant, and algae (e.g., *Chlamydomonas reinhardtii*). As used herein, the term "cereal crop" is used in its broadest sense. The term includes, but is not limited to, any species of grass, or grain plant (e.g., barley, corn, oats, rice, wild rice, rye, wheat, millet, sorghum, triticale, etc.), non-grass plants (e.g., buckwheat flax, legumes [soybeans] etc.). As used herein, the term "crop" or "crop plant" is used in its broadest sense. The term includes, but is not limited to, any species of plant or algae edible by humans or used as a feed for animals or used, or consumed by humans, or any plant or algae used in industry or commerce. As used herein, the term "dark-dier" refers to a class of mutant organisms strains that are obligate phototrophs, including but not limited to, mutant strains of *Chamydomonas reinhardtii*.

Algae, alga or the like, refer to plants belonging to the subphylum Algae of the phylum Thallophyta. There are over 40,000 wild algal species, but most leading companies genetically engineer or select the strains for oil production. Photosynthesizing algae require only photosynthesis, $CO_2$ and water which the plant uses to produce glucose and further metabolizes into lipids or oil as stored fuel for an uncertain future. The algae are unicellular, photosynthetic, and are non-parasitic plants without roots, stems or leaves. They contain chlorophyll and have a great variety of sizes, from microscopic to large seaweeds. Green algae, including Eukaryota, Viridiplantae, Chlorophyta, Chlorophyceae, are particularly useful in the invention. *C. reinhardtii* is a Volvocales—Chlamydomonadaceae. However, algae useful in the invention may also be blue-green, red, or brown, so long as the algae is able to produce fatty acids.

*Chlamydomonas* is a genus of unicellular green algae (Chlorophyta) that is found all over the world. More than 500 different species of *Chlamydomonas* are known, but the most widely used laboratory species is *Chlamydomonas reinhardtii*. *C. reinhardtii*, is a unicellular green algae that has been a useful model for many types of studies, including photosynthesis and motility. Photosynthesis, when light is available, and acetate when light is not, are involved in energy production and consumption in *C. Reinhardtii*.

The most common oil-producing algae can generally include, or consist essentially of, the diatoms (bacillariophytes), green algae (chlorophytes), blue-green algae (cyanophytes), and golden-brown algae (chrysophytes). In addition a fifth group known as haptophytes may be used. Specific non-limiting examples of bacillariophytes capable of oil production include the genera *Amphipleura, Amphora, Chaetoceros, Cyclotella, Cymbella, Fragilaria, Hantzschia, Navicula, Nitzschia, Phaeodactylum*, and *Thalassiosira*. Specific non-limiting examples of chlorophytes capable of oil production include *Ankistrodesmus, Botryococcus, Chlorella, Chlorococcum, Dunaliella, Monoraphidium, Oocystis, Scenedesmus*, and *Tetraselmis*. In one aspect, the chlorophytes can be *Chlorella* or *Dunaliella*. Specific non-limiting examples of cyanophytes capable of oil production include *Oscillatoria* and *Synechococcus*. A specific example of chrysophytes capable of oil production includes *Boekelovia*. Specific non-limiting examples of haptophytes include *Isochysis* and *Pleurochysis*. In one aspect, the oil-producing algae or plant cells can have oil content greater than about 20%, and preferably greater than about 30% or 40% or 50% by weight of the algae.

An oil-producing algae can be cultivated in a cultivation sub-system. Both autotrophic and heterotrophic growth can be used to produce a useful quantity of algae and for the algae to produce useful oil. The autotrophic growth and heterotrophic growth can also be sequentially performed in a multiple stage process. The algae can be grown in a greenhouse environment such as the raceway ponds as described above, although other growth environments may also be suitable. Non-limiting examples of growth environments or reservoirs which can be used include bioreactors, open ponds having various shapes and configurations.

Fungi, as used herein, refer to fungi capable of photosynthesis. An example of a photosynthesizing fungi is *Schizochytrium*, an algae-like, salt water/deep ocean fungus that fish consume. Fungus also include yeast and other autotrophic organisms.

Yeast are single celled fungi. Classification for yeast involves the characteristics of the cell, ascospore, colony, and physiological characteristics all of which are used to identify a particular species of yeast. A well-known characteristics is the ability to ferment sugars for the production of ethanol. Budding yeasts are fungi from Ascomycetes class; Saccharomycetes (also called Hemiascomycetes). The true yeasts are separated into one main order Saccharomycetales. The most well-known and commercially significant yeasts are the related species and strains of *Saccharomyces cerevisiae*.

Free energy consumed by biological systems originates as solar energy. Photosynthetic organisms have evolved the processes of photosynthesis to take advantage of the solar radiation reaching the earth. Essentially, photosynthesis is a light-induced redox process in which carbon dioxide is reduced to a metabolizable storage compound by an external reductant (i.e., light is used to create reducing potential). Photosynthetic organisms are primarily classified by the nature of the reductant used during photosynthetic processes. Oxygenic photosynthetic organisms, for instance, are distinguished from prokaryotic photosynthetic organisms primarily by their ability to use water as a reductant. Plants, algae, cyanobacteria, and prochlorophytes are all oxygenic photosynthetic organisms. Green plants photosynthesis takes place in chloroplasts. The systems that convert solar energy in green plants to useful metabolic energy are integrated into the thylakoid membrane system of green plant chloroplasts. In particular, the thylakoid membranes contain the energy-transducing machinery: the light-harvesting-proteins, reaction centers, electron transport chains, and ATP synthase. Photosynthesis in green plants begins by the absorption of light by a chlorophyll porphyrin (i.e., with a coordinated magnesium ion). The resulting electronic excitation passes along a series of chlorophyll molecules until the excitation is trapped in a reaction center. In the reaction center the energy of light (i.e., electron excitation) is converted into a separation of charge (i.e., reducing potential). Green plants use two light reactions: photosystem I and photosystem II. Photosystem I generates reducing potential in the form of NADPH. Photosystem II transfers the electrons of water to a quinone and concomitantly evolves diatomic oxygen. The flow of electrons in, and between, both photosystem generates a proton gradient across the thylakoid membrane that drives the synthesis of ATP. The ATP and NADPH that results from photophosphorylation processes in green plants are used to reduce carbon dioxide and convert it into 3-phosphoglycerate. The electron-motive force generated in green plant chloroplast photosystems drives electron transfer in a opposite direction from that in mitochondria. In photosynthesis, electrons are taken from water to produce diatomic oxygen, and concomitantly used to reduce carbon dioxide to synthesize carbohydrates. Chloroplasts, therefore, generate diatomic oxygen and carbohydrate, while mitochondria consume oxygen and carbohydrate.

The fungi or plant cells may be cultured in natural or artificial environments. The use of the word "culture" is meant to refer to the propagation of living cells in media that is conducive to growth under the appropriate environmental conditions. Thus, culture includes natural environments for oil producing cells such as plants and fungi. The most common non-natural or cultured media include broths, gelatin, and agar. The culture may be solid or liquid. Culturing may be done on a commercial scale, or in a single Petri dish.

The methods of the invention can be used on any oil producing cells. In some instances the oil producing cells are naïve (or untreated and not manipulated). In other instances, the oil producing cells may also be treated in order to promote increased production and or accumulation of fatty acids. One method for achieving this involves disrupting a fatty acid metabolism pathway, for instance, by contacting the oil producing cell with an inhibitor of fatty acid metabolism in an effective amount to promote accumulation or storage of fatty acids. Oil producing cells have several enzymes that are required for fatty acid oxidation, which once inhibited, results in storage and secretion of fatty acids. Thus, metabolic modifiers, including inhibitors such as small molecule and nucleic acid inhibitors as well as activators of specific metabolic processes, can increase the stored energy reserves in a broad spectrum of organisms, thereby increasing their use as biofuels.

Prior to the invention a study examined an enzyme involved in catalyzing a key metabolic step in the synthesis of oils in algae. This study is described in Sheehan et al (The US Department of Energy's Aquatic Species Program: Biodiesel from Algae (1998). A Look Back at the US Department of Energy's Aquatic Species Program—Biodiesel from Algae, U. D. o. E. s. O. o. F. Development, ed. (Golden, Colo., National Renewable Energy Laboratory)). Sheehan et al suggests that the discovery of this enzyme, referred to as Acetyl CoA Carboxylase (ACCase) led to hope that expression of the enzyme in algae would result in higher production levels of fatty acids for use as a biofuel. Although this enzyme was necessary for the metabolic process of oil production in algae, forced expression of the ACCase gene did not demonstrate increased oil production in the cells.

In contrast to this finding, Applicants have demonstrated that disrupting or inhibiting fatty acid metabolism in oil producing cells results in significantly increased oil production in these cells. Thus, in some aspects the invention relates to methods for promoting increased accumulation or storage of fatty acids in oil producing cells, and enhancing secretion using herbicides. Increased accumulation or storage refers to any increase with respect to an oil producing cell that has not been treated or altered according to the methods of the invention. The amount of fatty acids stored within a cell can be assessed by any methodology known in the art. For example methods for measuring fatty acid accumulation in a cell are described in the Examples section and include flow cytometry.

Other methods for enhancing oil production are well known in the art and are encompassed within the methods of the invention. For instance, algae may be altered by introduction of exogenous DNA such that fatty acid promoting proteins can be produced within the cell.

The term "disrupting a fatty acid metabolism pathway" as used herein refers to any interruption in the processing of cellular fatty acids. An interruption in the processing of cellular fatty acids leads to increased accumulation or storage of such fatty acids. Metabolic disruption of fatty acids can be achieved using inhibitors of fatty acid metabolism. A "fatty acid metabolism inhibitor," as used herein, is a compound able to inhibit (e.g., prevent, or at least decrease or inhibit the activity by an order of magnitude or more) a reaction within the fatty acid metabolism pathway, such as an enzyme-catalyzed reaction within the pathway. The inhibitor may inhibit the enzyme, e.g., by binding to the enzyme or otherwise interfering with operation of the enzyme (for example, by blocking an active site or a docking site, altering the configuration of the enzyme, competing with an enzyme substrate for the active site of an enzyme, etc.), and/or by reacting with a coenzyme, cofactor, etc. necessary for the enzyme to react with a substrate. The fatty acid metabolism pathway is the pathway by which fatty acids are metabolized within a cell for energy (e.g., through the synthesis of ATP and the breakdown of fatty acids into simpler structures, such as CO2, acyl groups, etc.) or to produce a carbohydrate source. For example inhibitors of fatty acid metabolism include inhibitors of fatty acid oxidation, fatty acid transporter inhibitors, reductase inhibitors, and isomerase inhibitors within the fatty acid metabolism pathway.

The fatty acid metabolism inhibitor in some embodiments is an inhibitor of fatty acid oxidation, a fatty acid transporter inhibitor, a reductase inhibitor, or an isomerase inhibitor within the fatty acid metabolism pathway. In one embodiment the reductase is 2,4-dienoyl-CoA reductase. In another embodiment the isomerase is 2,4-dienoyl-CoA isomerase. In yet other embodiments the inhibitor of fatty acid metabolism is an inhibitor of fatty acid oxidation and is any one or more of the following: oxirane carboxylic acid compound, such as etomoxir (2-(6-(4-chlorophenoxy)-hexyl)-oxirane-2-carboxylic acid ethyl ester), 2-(4-(3-chlorophenoxy)-butyl)-oxirane-2-carboxylic acid ethyl ester, 2-(4-(3-trifluoromethylphenoxy)-butyl)-oxirane-2-carboxylic acid ethyl ester, 2-(5(4-chlorophenoxy)-pentyl)-oxirane-2-carboxylic acid ethyl ester, 2-(6-(3,4-dichlorophenoxy)-hexyl)-oxirane-2-carboxylic acid ethyl ester, 2-(6-(4-fluorophenoxy)-hexyl)-oxirane-2-carboxylic acid ethyl ester, 2-(6-phenoxyhexyl)-oxirane-2-carboxylic acid ethyl ester, cerulenin, 5-(tetradecyloxy)-2-furoic acid, oxfenicine, methyl palmoxirate, metoprolol, amiodarone, perhexiline, aminocamitine, hydrazonopropionic acid, 4-bromocrotonic acid, trimetazidine, ranolazine, hypoglycin, dichloroacetate, methylene cyclopropyl acetic acid, beta-hydroxy butyrate, and a non-hydrolyzable analog of carnitine or pharmacologically acceptable salts thereof.

The fatty acid metabolism pathway includes several enzymatic reactions, which use various enzymes such as reductases or isomerases. Specific examples of enzymes within the fatty acid metabolism pathway include 2,4-dienoyl-CoA reductase, 2,4-dienoyl-CoA isomerase, butyryl dehydrogenase, etc, as further discussed below. In one embodiment, the fatty acid metabolism inhibitor is an inhibitor able to inhibit a beta-oxidation reaction in the fatty acid metabolism pathway. In another embodiment, the inhibitor is an inhibitor for a fatty acid transporter (e.g., a transporter that transports fatty acids into the cell, or from the cytoplasm into the mitochondria for metabolism). In yet another embodiment, the inhibitor may react or otherwise inhibit key steps within the fatty acid metabolism pathway. In still another embodiment, the inhibitor may be an inhibitor of fatty acids as a source of energy in the mitochondria. For example, the inhibitor may inhibit the breakdown of intermediates such as butyryl CoA, glutaryl CoA, or isovaleryl CoA.

2,4-dienoyl-CoA reductase is an enzyme within the fatty acid metabolism pathway that catalyzes reduction reactions involved in the metabolism of polyunsaturated fatty acids. Certain fatty acids are substrates for 2,4-dienoyl-CoA reductases located within the mitochondria. In some cases, fatty acids may be transported into the mitochondria through uncoupling proteins. The uncoupling protein may, in certain instances, increase the mitochondrial metabolism to increase the availability of fatty acids within the mitochondria and/or increase the throughput of beta-oxidation within the mitochondria.

The enzyme 2,4-dienoyl-CoA isomerase is an enzyme within the fatty acid metabolism pathway that catalyzes isomerization of certain fatty acids. One step in the metabolism of certain polyunsaturated fatty acids may be protective against reactive oxygen intermediates ("ROI"). Thus, by generating substrates and antagonists for the activity of 2,4-dienyol-CoA isomerase, the metabolic production of reactive oxygen intermediates may be enhanced and/or reduced. This, in turn, affects the levels of fatty acids in the cell.

Thus, it is to be understood that, as used herein, compounds useful for inhibiting fatty acid metabolism (i.e., "fatty acid metabolism inhibitors") are also useful for altering cellular production of reactive oxygen; compounds described in reference to fatty acid metabolism inhibition should also be understood herein to be able to alter reactive oxygen production within a cell. For example, by altering the ability of a cell to metabolize a fatty acid, the ability of the cell to produce reactive oxygen may also be affected, since one pathway for a cell to produce reactive oxygen intermediates is through the metabolism of fatty acids. Thus, in some cases, the production of reactive oxygen can be affected by exposing a cell to, or removing a cell from, a fatty acid metabolism inhibitor.

The inhibitor of fatty acid metabolism may be an inhibitory nucleic acid. The inhibitory nucleic acid may be, for instance, specific for an enzyme selected from the group consisting of 2,4-dienoyl-CoA reductase, 2,4-dienoyl-CoA isomerase, and butyryl dehydrogenase.

In other embodiments the inhibitor of fatty acid metabolism is oxamate. The oxamate may be, for instance an alkyl oxamate such as, ethyl oxamate or sodium oxamate. The oxamate compounds may have the following structure:

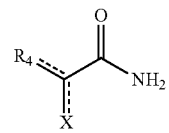

or a pharmaceutically acceptable salt or prodrug thereof, wherein $R_4$ is defined herein; wherein the dashed line is a double bond at one of the indicated positions and a single bond in the other; wherein $R_4$ is O—C—CH$_3$, —ONa, —OH, —O—(CH$_2$)$_3$—CH$_3$, —CH$_2$—C(O)—C(O)—O—$R_8$ or —CH=C(OH)—C(O)—O—$R_8$, alkyl, cycloalkyl, aryl, aralkyl, heteroaryl, heteroaralkyl, heterocyclyl, heterocycloalkyl, substituted alkyl, substituted cycloalkyl or substituted aryl, substituted aralkyl, substituted heteroaryl, substituted heteroaralkyl, substituted heterocyclyl, substituted heterocycloalkyl; wherein X is: =O, =N—OR$_2$; and wherein $R_2$ is independently selected from hydrogen, H$_2$, alkyl, cycloalkyl, aryl, substituted alkyl, substituted cycloalkyl or substituted aryl.

In some preferred embodiments the fatty acid inhibitor is an oxamate including, for example, each of the following:

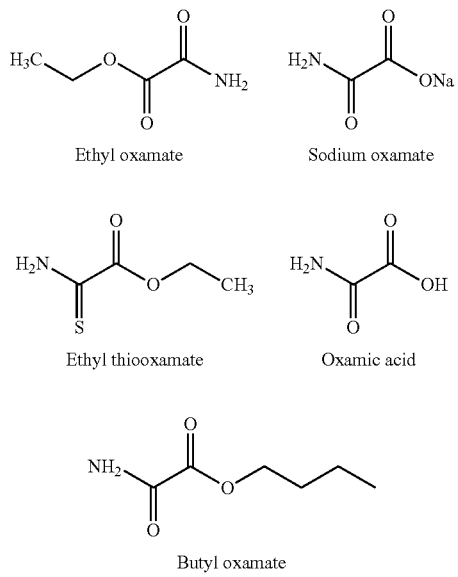

Ethyl oxamate    Sodium oxamate

Ethyl thiooxamate    Oxamic acid

Butyl oxamate

Pyruvate derivatives have been described in the art and are useful for inhibiting fatty acid production. For instance, US patents, such as U.S. Pat. Nos. 5,395,822; 6,916,850; 6,086,789; 5,968,727; 5,047,427 and 5,256,697 (the specific pyruvate derivatives, salts etc are incorporated by reference), describe pyruvate derivatives, conjugates and salts.

Fatty acid metabolism inhibitors also include an oxirane carboxylic acid compound or a pharmacologically acceptable salt thereof. In some embodiments the oxirane carboxylic acid compound has the formula:

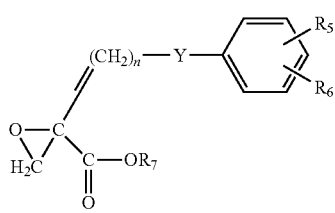

or a pharmaceutically acceptable salt or prodrug thereof, wherein $R_5$, $R_6$ and $R_7$ are herein; wherein $R_5$ represents a hydrogen atom, a halogen atom, a 1-4C alkyl group, a 1-4C alkoxy group, a nitro group or a trifluoromethyl group, $R_6$ has one of the meanings of $R_5$, $R_7$ represents a hydrogen atom or a 1-4C alkyl group, Y represents the grouping —O—$(CH_2)_m$—, m is 0 or a whole number from 1 to 4, and n is a whole number from 2 to 8 wherein the sum of m and n is a whole number from 2 to 8. $R_5$ in some embodiments is a halogen atom, $R_6$ is a hydrogen atom, m is 0, and n is 6. In other embodiments $R_7$ is an ethyl group. The oxirane carboxylic acid compound is etomoxir in some embodiments.

It is most particularly preferred to use etomoxir, i.e., 2-(6-(4-chlorophenoxy)-hexyl)-oxirane-2-carboxylic acid ethyl ester. Examples of other oxirane carboxylic acid compounds useful in the invention are 2-(4-(3-chlorophenoxy)-butyl)-oxirane-2-carboxylic acid ethyl ester, 2-(4-(3-trifluoromethylphenoxy)-butyl)-oxirane-2-carboxylic acid ethyl ester, 2-(5(4-chlorophenoxy)-pentyl)-oxirane-2-carboxylic acid ethyl ester, 2-(6-(3,4-dichlorophenoxy)-hexyl)-oxirane-2-carboxylic acid ethyl ester, 2-(6-(4-fluorophenoxy)-hexyl)-oxirane-2-carboxylic acid ethyl ester, and 2-(6-phenoxyhexyl)-oxirane-2-carboxylic acid ethyl ester, the corresponding oxirane carboxylic acids, and their pharmacologically acceptable salts.

The foregoing class of oxirane carboxylic acid compounds, including etomoxir, has been described by Horst Wolf and Klaus Eistetter in U.S. Pat. No. 4,946,866 for the prevention and treatment of illnesses associated with increased cholesterol and/or triglyceride concentration, and by Horst Wolf in U.S. Pat. No. 5,739,159 for treating heart insufficiency. The preparation of oxirane carboxylic acid compounds, and their use for blood glucose lowering effects as an ant diabetic agent, is described in Jew et al U.S. Pat. No. 6,013,666. Etomoxir has been described as an inhibitor of mitochondrial carnitine palmitoyl transferase-I by Mannaerts, G. P., L. J. Debeer, J. Thomas, and P. J. De Schepper "Mitochondrial and peroxisomal fatty acid oxidation in liver homogenates and isolated hepatocytes from control and clofibrate-treated rats," J. Biol. Chem. 254:4585-4595, 1979.

The foregoing U.S. Pat. Nos. 4,946,866, 5,739,159, and 6,013,666, United States Patent Application 20030036199, and the foregoing publication by Mannaerts, G. P., L. J. Debeer, J. Thomas, and P. J. De Schepper, are incorporated herein by reference. In addition, U.S. patent application Ser. No. 10/272,432, filed Oct. 15, 2002, entitled "Methods for Regulating Co-Stimulatory Molecule Expression with Reactive Oxygen," by M. K. Newell, et al. is incorporated herein by reference in its entirety.

Other, non-limiting examples of fatty acid metabolism inhibitors include fatty acid transporter inhibitors, beta-oxidation process inhibitors, reductase inhibitors, and/or isomerase inhibitors within the fatty acid metabolism pathway. Specific examples of other fatty acid metabolism inhibitors include, but are not limited to, cerulenin, 5-(tetradecyloxy)-2-furoic acid, oxfenicine, methyl palmoxirate, metoprolol, amiodarone, perhexiline, aminocamitine, hydrazonopropionic acid, 4-bromocrotonic acid, trimetazidine, ranolazine, hypoglycin, dichloroacetate, methylene cyclopropyl acetic acid, and beta-hydroxy butyrate. As another example, the inhibitor may be a non-hydrolyzable analog of camitine.

In one embodiment, the fatty acid metabolism inhibitor is a carboxylic acid. In some cases, the carboxylic acid may have the structure:

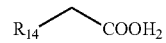

where $R_{14}$ comprises an organic moiety, as further described below. In some cases, $R_{14}$ may include at least two nitrogen atoms, or $R_{14}$ may include an aromatic moiety (as further described below), such as a benzene ring, a furan, etc.

In another embodiment, the fatty acid metabolism inhibitor has the structure:

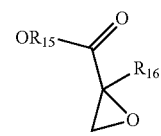

where each of $R_{15}$ and $R_{16}$ independently comprises organic moiety. In some instances, either or both of $R_{15}$ and $R_{16}$ may independently be an alkyl, such as a straight-chain alkyl, for instance, methyl, ethyl, propyl, etc. In certain cases, $R_{16}$ may have at least 5 carbon atoms, at least 10 carbon atoms, or at least 15 or more carbon atoms. For example, in one embodiment, $R_{16}$ may be a tetradecyl moiety. In other cases, $R^{16}$ may include an aromatic moiety, for example, a benzene ring. In still other cases, $R_{16}$ may have the structure:

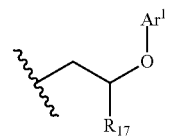

where $R^3$ comprises an organic moiety and $Ar^1$ comprises an aromatic moiety. $R_{17}$ may be a an alkyl, such as a straight-chain alkyl. In some instances, $Ar^1$ may be a benzene ring or a derivative thereof, i.e., having the structure:

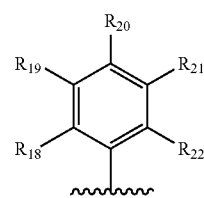

wherein each of $R_{18}$, $R_{19}$, $R_{20}$, $R_{21}$, and $R_{22}$ is hydrogen, a halogen, an alkyl, an alkoxy, etc.

In yet another embodiment, the fatty acid metabolism inhibitor has the structure:

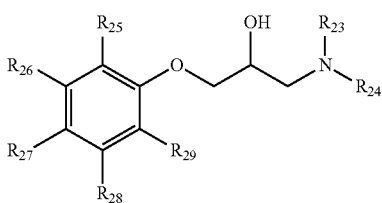

where each of $R_{23}$, $R_{24}$, $R_{25}$, $R_{26}$, $R_{27}$ $R_{28}$ and $R_{29}$ independently comprises hydrogen, a halogen, or an organic moiety, such as an alkyl, an alkoxy, etc. In some cases, $R_{23}$ and $R_{24}$ together may define an organic moiety, such as a cyclic group. For example, the fatty acid metabolism inhibitor may have the structure:

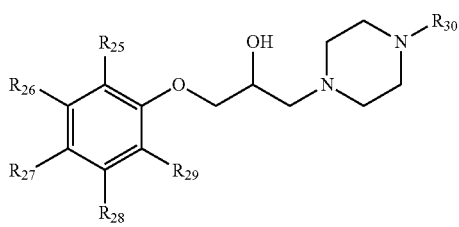

wherein $R_{30}$ comprises an organic moiety, such as an alkyl, an alkoxy, an aromatic moiety, an amide, etc. An example, of $R_{30}$ is:

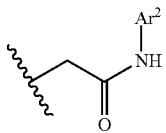

wherein $Ar^2$ comprises an aromatic moiety, such as a benzene ring or a benzene derivative, as previously described.

The molecules useful herein are isolated molecules. As used herein, the term "isolated" means that the referenced material is removed from its native environment, e.g., a cell or is synthetic. In either case it is not formulated with all of the materials with which it is ordinarily associated in nature. Thus, an isolated biological material can be free of some or all cellular components, i.e., components of the cells in which the native material is occurs naturally (e.g., cytoplasmic or membrane component). The isolated molecules may be substantially pure and essentially free of other substances with which they may be found in nature or in vivo systems to an extent practical and appropriate for their intended use. In particular, the molecules are sufficiently pure and are sufficiently free from other biological constituents of their hosts cells so as to be useful in, for example, producing pharmaceutical preparations or sequencing. Because an isolated peptide of the invention may be admixed with a pharmaceutically acceptable carrier in a pharmaceutical preparation, the peptide may comprise only a small percentage by weight of the preparation. The peptide is nonetheless substantially pure in that it has been substantially separated from the substances with which it may be associated in living systems. In some embodiments, the active agent of the invention is synthetic.

The term "purified" in reference to a compound such as a protein or a nucleic acid, refers to the separation of the desired substance from contaminants to a degree sufficient to allow the practitioner to use the purified substance for the desired purpose. Preferably this means at least one order of magnitude of purification is achieved, more preferably two or three orders of magnitude, most preferably four or five orders of magnitude of purification of the starting material or of the natural material. In specific embodiments, a purified active agent is at least 60%, at least 80%, or at least 90% of total protein or nucleic acid, as the case may be, by weight. In a specific embodiment, a purified active agent is purified to homogeneity as assayed by, e.g., sodium dodecyl sulfate polyacrylamide gel electrophoresis, or agarose gel electrophoresis.

Each of the compounds encompassed within chemical formulas described herein include single tautomers, single stereoisomers and mixtures of tautomers and/or stereoisomers, and the pharmaceutically acceptable salts thereof.

In addition to the inhibitors of fatty acid metabolism, the methods for preparing biofuels may be achieved using an inhibitor of UCP. As taught in U.S. Pat. No. 7,105,718 UCP is present in plant cellular membranes other than the mitochondrial membrane. For instance, UCP is expressed on the cell wall, plasma membrane and chloroplasts of light and cold sensitive cells but not of light and cold resistant cells. It is taught therein that inhibitors of UCP are useful for increasing the production of fatty acids in plant cells.

A variety of uncoupling proteins (UCPs) are known to exist in vertebrate and photosynthetic organisms. These proteins are named for the ability to dissipate the above described proton gradient generated by the respective electron transport chains in mammalian mitochondria and green plant chloroplasts. Thus, these proteins are said to uncouple the flow of protons across a membrane through ATP synthetase and prevent the concomitant production of ATP. Dissipation of the proton gradient in this manner produces heat in a process called thermogenesis.

UCP-like proteins occur in each of the four eukaryotic kingdoms: animals, plants, fungi, and protists (See e.g., Jarmuszkiewicz et al., FEBS Lett., 467:145 [2000].) UCPs are encoded by small multi-gene families in both mammals and plants. In mammals, UCP1 is exclusively expressed in brown adipocyte tissue, while UCP2 is expressed in most tissues of humans and rodents (See e.g., Boss et al., Eur. J. of Endorinol. 139, 1-9 [1998]); UCP3 is expressed in both skeletal muscle and in human brown adipoctye tissue (See e.g., Vidal-Puig et al., Biochem. Biophys. Res. Com 235:79 [1997]); and UCP4 is expressed in brain tissues. In mammals, UCP causes a change from glucose to fatty acid oxidation in mitochondria, and consequent thermogenesis in brown adipocyte tissue.

Plant UCP was first identified in potato tuber and has been isolated in *Arabidopsis*. These potato UCP are located in the mitochondria and have been implicated in chill resistance in plants (See e.g., Nantes et al., FEBS Lett., 457:103 [1999].

The present invention, while not intended to be limited by the selection of a particular uncoupling protein sequences, provides a variety of UCP gene or mRNA sequences, including, but not limited to, 1) plant UCPs: Genbank accession AJ002586 (*Solanum tuberosum* "potato,"), AJ223983 (*Arabidopsis thaliana*), AB021706 (*Arabidopsis thaliana*), AB024733 (*Symplocarpus renifoliu* "skunk cabbage"); 2) human UCPs: U28480 (UCP), AF096289 (UCP2), AF019409 (UCP2), U7637 (UCP2), AF011449 (UCP2), AF001787 (UCP3), 008476367 (UCP3), AF1104532 (UCP4); 3) mouse UCPs: AAB17666 (UCP), U63418 (UCP), U63419 (UCP), AF096288 (UCP2), AB012159 (UCP2), U69135 (UCP2), AF032902 (UCP3), AF053352 (UCP3), AF030164 (UCP3), AB010742 (UCP3); 4) rat UCPs: NM012682 (UCP), X03894 (UCP), X12925 (UCP), M11814 (UCP), AF039033 (UCP2), AB010743 (UCP2), AB005143 (UCP2), AB006613 (UCP2), AF030163 (UCP3), AB008216 (UCP3), AF035943 (UCP3), AB006614 (UCP3), U92069 (UCP3); 5) pig UCPs: AF111998 (UCP2), 111999 (UCP2), AF036757 (UCP2), A128837 (UCP3), AF095744 (UCP3); 6) cow UCPs: AF092048 (UCP3); 7) dog UCPs: AB020887 (UCP2), AB022020 (UCP3); and 8) rabbit UCP X14696.

The UCP activity may be modified with the use of UCP inhibitors. "UCP activity" refers to an induction of expression of new or exogenous UCP, modulation of the activity of existing UCP, or the translocation of existing sources of UCP to different membranes.

UCP inhibitors are any compounds which decrease the activity of UCP in the cell. UCP inhibitors include but are not limited to UCP binding peptides such as anti-UCP antibodies, UCP anti-sense nucleic acids, UCP RNAi, UCP dominant negative nucleic acids, nucleotides, nucleotide analogs, tocopherols, such as tocotrienols, and non omega 3 or 6 fatty acids. Other types of inhibitors include ribozymes which interfere with the transcription, processing, or translation of UCP mRNA. In other embodiments the UCP inhibitor is tunicamycin. Tunicamycin promotes intracellular trafficking of the UCP between intracellular locations. Each of these inhibitors is well known in the art and has been described extensively in the literature.

Nucleotides and nucleotide (purine and pyrimidine) analogs include but are not limited to guanosine diphosphate (GDP). Purine analogs include but are not limited to guanosine diphosphate, 8-oxo-Adenosine, 8-oxo-Guanosine, 8-fluoro-Adenosine, 8-fluoro-Guanosine, 8-methoxy-Adenosine, 8-methoxy-Guanosine, 8-aza-Adenosine and 8-aza-Guanosine, azacitidine, Fludarabine phosphate, 6-MP, 6-TG, azathioprine, allopurinol, acyclovir, gancylovir, deoxycoformycin, and arabinosyladienine (ara-A), guanosine diphosphate fucose, guanosine diphosphate-2-fluorofucose, guanosine diphosphate-.beta.L-2-aminofucose, guanosine diphosphate-D-arabinose and 2-aminoadenosine. Some examples of pyrimidine analogues are uracil, thymine, cytosine, 5-fluorouracil, 5-chlorouracil, 5-bromouracil, dihydrouracil, 5-methylcytosine, 5-propynylthymine, 5-propynyluracil and 5-propynylcytosine, 5-fluorocytosine, Floxuridine, uridine, thymine, 3'-azido-3'-deoxythymidine, 2-fluorodeoxycytidine, 3-fluoro-3'-deoxythymidine; 3'-dideoxycytidin-2'-ene; and 3'-deoxy-3'-deoxythymidin-2'-ene, cytosine arabinoside. Other such compounds are known to those of skill in the art.

UCP inhibitors also include UCP binding peptides or molecules. The binding peptides or molecules can be delivered directly to the cell to act on the UCP. The UCP binding peptides and molecules of the invention can be identified using routine assays, such as the binding and activation assays.

The UCP binding molecules may be isolated from natural sources or synthesized or produced by recombinant means. Methods for preparing or identifying molecules which bind to a particular target are well-known in the art. Molecular imprinting, for instance, may be used for the de novo construction of macro molecular structures, such as peptides, which bind to a particular molecule. See for example, Kenneth J. Shea, *Molecular Imprinting of Synthetic Network Polymers: The De novo Synthesis of Molecular Binding In Catalytic Sites*, Trip, to May 1994; Klaus, Mosbach, Molecular Imprinting, Trends in *Biochem. Sci.*, 19(9), January 1994; and Wulff, G., In Polymeric Reagents and Catalysts (Ford, W. T., ed.) *ACS Symposium Series* No. 308, P. 186-230, *Am. Chem. Soc.* 1986. Binding peptides, such as antibodies, may easily be prepared by generating antibodies to UCP (or obtained from commercial sources) or by screening libraries to identify peptides or other compounds which bind to the UCP.

Many UCP antibodies are commercially available. These include but are not limited to those antibodies commercially available from Santa Cruz Biotechnology, Inc., e.g., UCP1 (m-17, sc-6529), UCP1 (C-17, sc-6528), UCP2 (A19, sc-6527), UCP2 (N19, sc-6526), UCP2 (c-20, sc-6525), and UCP3 (C-20, sc-7756); antibodies commercially available from Research Diagnostics Inc e.g., Goat anti-UCP1 HUMAN/Mouse/Rat (cat#RDI-UCP1Cabg); Goat anti-UCP1 HUMAN/Mouse/Rat (cat#RDI-MUCP1Cabg); Goat anti-UCP2 HUMAN/Mouse/Rat (cat#RDI-UCP2Nabg); Goat anti-UCP2 HUMAN/Mouse/Rat (cat#RDI-UCP2Cabg); Goat anti-UCP2 HUMAN/Mouse/Rat (cat#RDI-UCP2C1abg); Rabbit anti-Murine UCP1 (cat#RDI-MUCP12abrX); Rabbit anti-Murine UCP1 (cat#RDI-MUCP19abrX); Rabbit anti-Murine UCP2 (cat#RDI-MUCP2abrX); Rabbit anti-Murine UCP2 (cat#RDI-MUCP2CabrX); Rabbit anti-human UCP2 (cat#RDI-UCP2MabrX); UCP3L (see Boss, 0 et al (1997) FEBS Lett 408, 38-42; Vidal-Plug A et al (1997) BBRC 235, 79-82); Rabbit anti-HUMAN UCP3 (cat#RDI-UCP3abrX); Rabbit anti-HUMAN UCP3 (cat#RDI-UCP3CbrX); Rabbit anti-HUMAN UCP3 (cat#RDI-UCP3MabrX); Rabbit anti-Rat UCP3 (cat#RDI-RTUCP3MabrX), etc.

In one embodiment the binding peptides useful according to the invention are antibodies or functionally active antibody fragments. As used herein, the term "antibody" means not only intact antibody molecules but also fragments of antibody molecules retaining specific binding ability. Such fragments are also well known in the art. In particular, as used herein, the term "antibody" means not only intact immunoglobulin molecules but also the well-known active fragments $F(ab')_2$, and Fab. $F(ab')_2$, and Fab fragments which lack the Fc fragment of intact antibody (Wahl et al., *J. Nucl. Med.* 24:316-325 (1983)).

In another set of embodiments, the cells may be exposed to an agent that inhibits the synthesis or production of one or more enzymes within the fatty acid metabolism pathway or other gene encoding a protein that plays a positive role in fatty acid metabolism.

Thus, the invention also features the use of small nucleic acid molecules, including antisense nucleic acids and short interfering nucleic acid (siNA), the latter include, for example: microRNA (miRNA), short interfering RNA (siRNA), double-stranded RNA (dsRNA), and short hairpin RNA (shRNA) molecules to knockdown expression of proteins such as enzymes involved in fatty acid metabolism. An siNA of the invention can be unmodified or chemically-modified. An siNA of the instant invention can be chemically synthesized, expressed from a vector or enzymatically synthesized. The instant invention also features various chemically-modified synthetic short interfering nucleic acid (siNA) molecules capable of modulating gene expression or activity in cells by RNA interference (RNAi). The use of chemically-modified siNA improves various properties of native siNA molecules through, for example, increased resistance to nuclease degradation in vivo and/or through improved cellular uptake. Furthermore, siNA having multiple chemical modifications may retain its RNAi activity.

The siNA molecules of the instant invention provide useful reagents and methods for a variety of therapeutic applications.

Chemically synthesizing nucleic acid molecules with modifications (base, sugar and/or phosphate) that prevent their degradation by serum ribonucleases can increase their potency (see e.g., Eckstein et al., International Publication No. WO 92/07065; Perrault et al, 1990 Nature 344, 565; Pieken et al., 1991, Science 253, 314; Usman and Cedergren, 1992, Trends in Biochem. Sci. 17, 334; Usman et al., International Publication No. WO 93/15187; and Rossi et al., International Publication No. WO 91/03162; Sproat, U.S. Pat. No. 5,334,711; and Burgin et al., supra; all of these describe various chemical modifications that can be made to the base, phosphate and/or sugar moieties of the nucleic acid molecules herein). Modifications which enhance their efficacy in cells, and removal of bases from nucleic acid molecules to shorten oligonucleotide synthesis times and reduce chemical requirements are desired. (All these publications are hereby incorporated by reference herein).

There are several examples in the art describing sugar, base and phosphate modifications that can be introduced into nucleic acid molecules with significant enhancement in their nuclease stability and efficacy. For example, oligonucleotides are modified to enhance stability and/or enhance biological activity by modification with nuclease resistant groups, for example, 2'amino, 2'-C-allyl, 2'-flouro, 2'-O-methyl, 2'-H, nucleotide base modifications (for a review see Usman and Cedergren, 1992, TIBS. 17, 34; Usman et al., 1994, Nucleic Acids Symp. Ser. 31, 163; Burgin et al., 1996, Biochemistry, 35, 14090). Sugar modification of nucleic acid molecules have been extensively described in the art (see Eckstein et al., International Publication PCT No. WO 92/07065; Perrault et al. Nature, 1990, 344, 565 568; Pieken et al. Science, 1991, 253, 314317; Usman and Cedergren, Trends in Biochem. Sci., 1992, 17, 334 339; Usman et al. International Publication PCT No. WO 93/15187; Sproat, U.S. Pat. No. 5,334,711 and Beigelman et al., 1995, J. Biol. Chem., 270, 25702; Beigelman et al., International PCT publication No. WO 97/26270; Beigelman et al., U.S. Pat. No. 5,716,824; Usman et al., molecule comprises one or more chemical modifications.

In one embodiment, one of the strands of the double-stranded siNA molecule comprises a nucleotide sequence that is complementary to a nucleotide sequence of a target RNA or a portion thereof, and the second strand of the double-stranded siNA molecule comprises a nucleotide sequence identical to the nucleotide sequence or a portion thereof of the targeted RNA. In another embodiment, one of the strands of the double-stranded siNA molecule comprises a nucleotide sequence that is substantially complementary to a nucleotide sequence of a target RNA or a portion thereof, and the second strand of the double-stranded siNA molecule comprises a nucleotide sequence substantially similar to the nucleotide sequence or a portion thereof of the target RNA. In another embodiment, each strand of the siNA molecule comprises about 19 to about 25 nucleotides, and each strand comprises at least about 19 nucleotides that are complementary to the nucleotides of the other strand.

In some embodiments an siNA is an shRNA, shRNA-mir, or microRNA molecule encoded by and expressed from a genomically integrated transgene or a plasmid-based expression vector. Thus, in some embodiments a molecule capable of inhibiting mRNA expression, or microRNA activity, is a transgene or plasmid-based expression vector that encodes a small-interfering nucleic acid. Such transgenes and expression vectors can employ either polymerase II or polymerase III promoters to drive expression of these shRNAs and result in functional siRNAs in cells. The former polymerase permits the use of classic protein expression strategies, including inducible and tissue-specific expression systems. In some embodiments, transgenes and expression vectors are controlled by tissue specific promoters. In other embodiments transgenes and expression vectors are controlled by inducible promoters, such as tetracycline inducible expression systems.

In another embodiment, a small interfering nucleic acid of the invention is expressed in plant or fungal cells using a plant, fungal or mammalian expression vectors. The recombinant expression vector may be capable of directing expression of the nucleic acid preferentially in a particular cell type (e.g., tissue-specific regulatory elements are used to express the nucleic acid). Tissue specific regulatory elements are known in the art.

Other inhibitor molecules that can be used include sense and antisense nucleic acids (single or double stranded), ribozymes, peptides, DNAzymes, peptide nucleic acids (PNAs), triple helix forming oligonucleotides, antibodies, and aptamers and modified form(s) thereof directed to sequences in gene(s), RNA transcripts, or proteins. Antisense and ribozyme suppression strategies have led to the reversal of a tumor phenotype by reducing expression of a gene product or by cleaving a mutant transcript at the site of the mutation (Carter and Lemoine Br. J. Cancer. 67(5):869-76, 1993; Lange et al., Leukemia. 6(11):1786-94, 1993; Valera et al., J. Biol. Chem. 269(46):28543-6, 1994; Dosaka-Akita et al., Am. J. Clin. Pathol. 102(5):660-4, 1994; Feng et al., Cancer Res. 55(10):2024-8, 1995; Quattrone et al., Cancer Res. 55(1):90-5, 1995; Lewin et al., Nat Med. 4(8):967-71, 1998). For example, neoplastic reversion was obtained using a ribozyme targeted to an H-Ras mutation in bladder carcinoma cells (Feng et al., Cancer Res. 55(10): 2024-8, 1995). Ribozymes have also been proposed as a means of both inhibiting gene expression of a mutant gene and of correcting the mutant by targeted trans-splicing (Sullenger and Cech Nature 371(6498):619-22, 1994; Jones et al., Nat. Med. 2(6):643-8, 1996). Ribozyme activity may be augmented by the use of, for example, non-specific nucleic acid binding proteins or facilitator oligonucleotides (Herschlag et al., Embo J. 13(12):2913-24, 1994; Jankowsky and Schwenzer Nucleic Acids Res. 24(3):423-9, 1996). Multitarget ribozymes (connected or shotgun) have been suggested as a means of improving efficiency of ribozymes for gene suppression (Ohkawa et al., Nucleic Acids Symp Ser. (29):121-2, 1993).

Antisense nucleic acids include modified or unmodified RNA, DNA, or mixed polymer nucleic acids, and primarily function by specifically binding to matching sequences resulting in modulation of peptide synthesis (Wu-Pong, November 1994, BioPharm, 20-33). Antisense nucleic acid binds to target RNA by Watson Crick base-pairing and blocks gene expression by preventing ribosomal translation of the bound sequences either by steric blocking or by activating RNase H enzyme. Antisense molecules may also alter protein synthesis by interfering with RNA processing or transport from the nucleus into the cytoplasm (Mukhopadhyay & Roth, 1996, Crit. Rev. in Oncogenesis 7, 151-190).

As used herein, the term "antisense nucleic acid" describes a nucleic acid that is an oligoribonucleotide, oligodeoxyribonucleotide, modified oligoribonucleotide, or modified oligodeoxyribonucleotide which hybridizes under physiological conditions to DNA comprising a particular gene or to an mRNA transcript of that gene and, thereby, inhibits the transcription of that gene and/or the translation of that mRNA. The antisense molecules are designed so as to interfere with transcription or translation of a target gene upon hybridization with the target gene or transcript. Those skilled in the art will recognize that the exact length of the antisense oligonucleotide and its degree of complementarity with its target will depend upon the specific target selected, including the sequence of the target and the particular bases which comprise that sequence.

Triple helix approaches have also been investigated for sequence-specific gene suppression. Triple helix forming oligonucleotides have been found in some cases to bind in a sequence-specific manner (Postel et al., Proc. Natl. Acad. Sci. U.S.A. 88(18):8227-31, 1991; Duval-Valentin et al., Proc. Natl. Acad. Sci. U.S.A. 89(2):504-8, 1992; Hardenbol and Van Dyke Proc. Natl. Acad. Sci. U.S.A. 93(7):2811-6, 1996; Porumb et al., Cancer Res. 56(3):515-22, 1996). Similarly, peptide nucleic acids have been shown to inhibit gene expression (Hanvey et al., Antisense Res. Dev. 1(4): 307-17, 1991; Knudsen and Nielson Nucleic Acids Res. 24(3):494-500, 1996; Taylor et al., Arch. Surg. 132(11): 1177-83, 1997). Minor-groove binding polyamides can bind in a sequence-specific manner to DNA targets and hence may represent useful small molecules for future suppression at the DNA level (Trauger et al., Chem. Biol. 3(5):369-77, 1996). In addition, suppression has been obtained by interference at the protein level using dominant negative mutant peptides and antibodies (Herskowitz Nature 329(6136):219-22, 1987; Rimsky et al., Nature 341(6241):453-6, 1989; Wright et al., Proc. Natl. Acad. Sci. U.S.A. 86(9):3199-203, 1989). In some cases suppression strategies have led to a reduction in RNA levels without a concomitant reduction in proteins, whereas in others, reductions in RNA have been mirrored by reductions in protein.

The diverse array of suppression strategies that can be employed includes the use of DNA and/or RNA aptamers that can be selected to target, for example, a protein of interest such as enzymes involved in fatty acid metabolism.

Many embodiments of the invention employ single-stranded RNA molecules containing an inverted repeat region that causes the RNA to self-hybridize, forming a hairpin structure. shRNA molecules of this type may be encoded in RNA or DNA vectors. The term "encoded" is used to indicate that the vector, when acted upon by an appropriate enzyme, such as an RNA polymerase, will give rise to the desired shRNA molecules (although additional processing enzymes may also be involved in producing the encoded shRNA molecules). As described herein, vectors comprising one or more encoded shRNAs may be transfected into cells ex vivo, and the cells may be introduced into mammals. The expression of shRNAs may be constitutive or regulated in a desired manner.

A double-stranded structure of an shRNA is formed by a single self-complementary RNA strand. RNA duplex formation may be initiated either inside or outside the cell. Inhibition is sequence-specific in that nucleotide sequences corresponding to the duplex region of the RNA are targeted for genetic inhibition. shRNA constructs containing a nucleotide sequence identical to a portion, of either coding or non-coding sequence, of the target gene are preferred for inhibition. RNA sequences with insertions, deletions, and single point mutations relative to the target sequence have also been found to be effective for inhibition. Because 100% sequence identity between the RNA and the target gene is not required to practice the present invention, the invention has the advantage of being able to tolerate sequence variations that might be expected due to genetic mutation, strain polymorphism, or evolutionary divergence. Sequence identity may be optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). Greater than 90% sequence identity, or even 100% sequence identity, between the inhibitory RNA and the portion of the target gene is preferred. Alternatively, the duplex region of the RNA may be defined functionally as a nucleotide sequence that is capable of hybridizing with a portion of the target gene transcript (e.g., 400 mM NaCl, 40 mM PIPES pH 6.4, 1 mM EDTA, 50° C. or 70° C. hybridization for 12-16 hours; followed by washing). In certain preferred embodiments, the length of the duplex-forming portion of an shRNA is at least 20, 21 or 22 nucleotides in length, e.g., corresponding in size to RNA products produced by Dicer-dependent cleavage. In certain embodiments, the shRNA construct is at least 25, 50, 100, 200, 300 or 400 bases in length. In certain embodiments, the shRNA construct is 400-800 bases in length. shRNA constructs are highly tolerant of variation in loop sequence and loop size.

The term "percent identical" refers to sequence identity between two amino acid sequences or between two nucleotide sequences. Percent identity can be determined by comparing a position in each sequence which may be aligned for purposes of comparison. Expression as a percentage of identity refers to a function of the number of identical amino acids or nucleic acids at positions shared by the compared sequences. Various alignment algorithms and/or programs may be used, including FASTA, BLAST, or ENTREZ. FASTA and BLAST are available as a part of the GCG sequence analysis package (University of Wisconsin, Madison, Wis.), and can be used with, e.g., default settings. ENTREZ is available through the National Center for Biotechnology Information, National Library of Medicine, National Institutes of Health, Bethesda, Md. In one embodiment, the percent identity of two sequences can be determined by the GCG program with a gap weight of 1, e.g., each amino acid gap is weighted as if it were a single amino acid or nucleotide mismatch between the two sequences.

Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. Preferably, an alignment program that permits gaps in the sequence is utilized to align the sequences. The Smith-Waterman is one type of algorithm that permits gaps in sequence alignments. See Meth. Mol. Biol. 70: 173-187 (1997). Also, the GAP program using the Needleman and Wunsch alignment method can be utilized to align sequences. An alternative search strategy uses MPSRCH software, which runs on a MASPAR computer. MPSRCH uses a Smith-Waterman algorithm to score sequences on a massively parallel computer. This approach improves ability to pick up distantly related matches, and is especially tolerant of small gaps and nucleotide sequence errors. Nucleic acid-encoded amino acid sequences can be used to search both protein and DNA databases.

An endogenous RNA polymerase of the cell may mediate transcription of an shRNA encoded in a nucleic acid construct. The shRNA construct may also be synthesized by a bacteriophage RNA polymerase (e.g., T3, T7, SP6) that is expressed in the cell. In preferred embodiments, expression of an shRNA is regulated by an RNA polymerase III promoters; such promoters are known to produce efficient silencing. A U6 snRNA leader sequence may be appended to the primary transcript; such leader sequences tend to increase the efficiency of sub-optimal shRNAs while generally having little or no effect on efficient shRNAs. For transcription from a transgene in vivo, a regulatory region (e.g., promoter, enhancer, silencer, splice donor and acceptor, polyadenylation) may be used to regulate expression of the shRNA strand (or strands). Inhibition may be controlled by specific transcription in an organ, tissue, or cell type; stimulation of an environmental condition (e.g., infection, stress, temperature, chemical inducers); and/or engineering transcription at a developmental stage or age. The RNA strands may or may not be polyadenylated; the RNA strands may or may not be capable of being translated into a polypeptide by a cell's translational apparatus. The use and production of an expression construct are known in the art (see also WO 97/32016; U.S. Pat. Nos. 5,593,874, 5,698, 425, 5,712,135, 5,789,214, and 5,804,693; and the references cited therein).

Further information on the optimization of shRNA constructs may be found, for example, in the following references: Paddison, P. J., A. A. Caudy, and G. J. Hannon, Stable suppression of gene expression by RNAi in mammalian cells. Proc Natl Acad Sci USA, 2002. 99(3): p. 1443-8; 13. Brummelkamp, T. R., R. Bernards, and R. Agami, A System for Stable Expression of Short Interfering RNAs in Mammalian Cells. Science, 2002. 21: p. 21; Kawasaki, H. and K. Taira, Short hairpin type of dsRNAs that are controlled by tRNA(Val) promoter significantly induce RNAi-mediated gene silencing in the cytoplasm of human cells. Nucleic Acids Res, 2003. 31(2): p. 700-7; Lee, N. S., et al., Expression of small interfering RNAs targeted against HIV-1 rev transcripts in human cells. Nat Biotechnol, 2002. 20(5): p. 500-5; Miyagishi, M. and K. Taira, U6 promoter-driven siRNAs with four uridine 3' overhangs efficiently suppress targeted gene expression in mammalian cells. Nat Biotechnol, 2002. 20(5): p. 497-500; Paul, C. P., et al., Effective expression of small interfering RNA in human cells. Nat Biotechnol, 2002. 20(5): p. 505-8.

An siNA useful in the invention will generally be designed to have partial or complete complementarity with one or more target genes (i.e., complementarity with one or more transcripts of one or more target genes). The target gene may be a gene derived from the cell, an endogenous gene, a transgene, or a gene of a pathogen which is present in the cell after infection thereof. Depending on the particular target gene, the nature of the siNA and the level of expression of siNA (e.g. depending on copy number, promoter strength) the procedure may provide partial or complete loss of function for the target gene. Quantitation of gene expression in a cell may show similar amounts of inhibition at the level of accumulation of target mRNA or translation of target protein.

"Inhibition of gene expression" refers to the absence or observable decrease in the level of protein and/or mRNA product from a target gene. "Specificity" refers to the ability to inhibit the target gene without manifest effects on other genes of the cell. The consequences of inhibition can be confirmed by examination of the outward properties of the cell or organism (as presented below in the examples) or by biochemical techniques such as RNA solution hybridization, nuclease protection, Northern hybridization, reverse transcription, gene expression monitoring with a microarray, antibody binding, enzyme linked immunosorbent assay (ELISA), Western blotting, radioimmunoassay (RIA), other immunoassays, and fluorescence activated cell analysis (FACS). For RNA-mediated inhibition in a cell line or whole organism, gene expression is conveniently assayed by use of a reporter or drug resistance gene whose protein product is easily assayed. Such reporter genes include acetohydroxyacid synthase (AHAS), alkaline phosphatase (AP), beta galactosidase (LacZ), beta glucoronidase (GUS), chloramphenicol acetyltransferase (CAT), green fluorescent protein (GFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentamycin, hygromycin, kanamycin, lincomycin, methotrexate, phosphinothricin, puromycin, and tetracyclin. One preferred method of assessing the function of an siNA of the invention involves determining changes in fat accumulation levels within a cell Depending on the assay, quantitation of the amount of gene expression allows one to determine a degree of inhibition which is greater than 10%, 33%, 50%, 90%, 95% or 99% as compared to a cell not treated according to the present invention. As an example, the efficiency of inhibition may be determined by assessing the amount of gene product in the cell: mRNA may be detected with a hybridization probe having a nucleotide sequence outside the region used for the inhibitory double-stranded RNA, or translated polypeptide may be detected with an antibody raised against the polypeptide sequence of that region.

As disclosed herein, the present invention is not limited to any type of target gene or nucleotide sequence. The following possible target genes are listed for illustrative purposes: specific examples of enzymes within the fatty acid metabolism pathway including 2,4-dienoyl-CoA reductase, 2,4-dienoyl-CoA isomerase, and butyryl dehydrogenase, as well as UCP. 2,4-dienoyl-CoA reductase has been described in for instance Koivuranta et al Biochemical Journal 1994, 304, p. 787. It is also disclosed in NCBI gene ID 1666 (DECR1) as well as NCBI genbank Accession number U78302 (SEQ ID NO. 1). The sequence of 2,4-dienoyl-CoA isomerase is disclosed in NCBI gene ID 1891 (ECH1).

| SEQ ID NO. | Sequence information | Sequence |
|---|---|---|
| 1 | Nucleic acid sequence for 2,4-dienoyl-CoA reductase | taagctttaa aaacatgtaa aaaggacatt aaattgacat cttttttgtg ttaggtcacc aaggagcagt gggacaccat agaagaactc atcaggaaga caaaaggttc ctaagaccac tttggccttc atcttggtta cagaaaaggg aatagaaatg aaacaaatta tctctcatct tttgactatt tcaagtctaa taaattctta attaacaaac attcattgaa tatgtattat gtgccaggcc agtgatagcc attgtatatt caaagataaa taaaatgaaa tatagtcttc aaaacattaa aaaaaaaagg agggcatggg gagagtaggt aaaggctcct ctttacctattt |
| 2 | Amino acid sequence for 2,4-dienoyl-CoA reductase | MKLPARVFFTLGSRLPCGLAPRRFFSYGTKILYQ NTEALQSKFFSPLQKAMLPPNSFQGKVAFITGGG TGLGKGMTTLLSSLGAQCVIASRKMDVLKATAEQ ISSQTGNKVHAIQCDVRDPDMVQNTVSELIKVAG HPNIVINNAAGNFISPTERLSPNAWKTITDIVLN GTAFVTLEIGKQLIKAQKGAAFLSITTIYAETGS GFVVPSASAKAGVEAMSKSLAAEWGKYGMRFNVI QPGPIKTKGAFSRLDPTGTFEKEMIGRIPCGRLG TVEELANLAAFLCSDYASWINGAVIKFDGGEEVL ISGEFNDLRKVTKEQWDTIEELIRKTKG |

In certain embodiments, a vector system for introducing siNA constructs into cells are retroviral vector systems, such as lentiviral vector systems. Lentiviral systems permit the delivery and expression of siNA constructs to both dividing and non-dividing cell populations in vitro and in vivo. Examples of Lentiviral vectors are those based on HIV, FIV and EIAV. See, e.g., Lois, C., et al., Germline transmission and tissue-specific expression of transgenes delivered by lentiviral vectors. Science, 2002. 295(5556): p. 868-72. Most viral systems contain cis-acting elements necessary for packaging, while trans-acting factors are supplied by a separate plasmid that is co-transfected with the vector into a packaging cell line. In certain embodiments, a highly transfectable 293 cell line may be used for packaging vectors, and viruses may be pseudotyped with a VSV-G envelope glycoprotein for enhanced stability and to provide broad host range for infection. In certain aspects, the invention provides novel vectors adapted for use with siNA expression cassettes. The type of vector and promoters to be employed should be selected, in part, depending on the organism and cell type to be affected.

In certain embodiments, retroviruses from which the retroviral plasmid vectors may be derived include, but are not limited to, Moloney Murine Leukemia Virus, spleen necrosis virus, Rous sarcoma Virus, Harvey Sarcoma Virus, avian leukosis virus, gibbon ape leukemia virus, human immunodeficiency virus, Myeloproliferative Sarcoma Virus, and mammary tumor virus. A retroviral plasmid vector may be employed to transduce packaging cell lines to form producer cell lines. Examples of packaging cells which may be transfected include, but are not limited to, the PE501, PA317, R-2, R-AM, PA12, T19-14.times., VT-19-17-H2, RCRE, RCRIP, GP+E-86, GP+envAm12, and DAN cell lines as described in Miller, Human Gene Therapy 1:5-14 (1990), which is incorporated herein by reference in its entirety. The vector may transduce the packaging cells through any means known in the art.

Essentially any method for introducing a nucleic acid construct into cells may be employed. Physical methods of introducing nucleic acids include injection of a solution containing the construct, bombardment by particles covered by the construct, soaking a cell, tissue sample or organism in a solution of the nucleic acid, or electroporation of cell membranes in the presence of the construct. A viral construct packaged into a viral particle may be used to accomplish both efficient introduction of an expression construct into the cell and transcription of the encoded shRNA. Other methods known in the art for introducing nucleic acids to cells may be used, such as lipid-mediated carrier transport, chemical mediated transport, such as calcium phosphate, and the like. Thus the siNA-encoding nucleic acid construct may be introduced along with components that perform one or more of the following activities: enhance RNA uptake by the cell, promote annealing of the duplex strands, stabilize the annealed strands, or otherwise increase inhibition of the target gene.

Thus, the present invention provides methods and compositions for the expression of nucleic acids including siNA in plants. The present invention contemplates that any method of transfection that is suitable for transfection of plants, plant tissues, and plant cells may be used with the present invention. Such methods include, but are not limited to, *Agrobacterium*-mediated transformation (e.g., Komari et al., Curr. Opin. Plant Biol., 1:161 [1998]), particle bombardment mediated transformation (e.g., Finer et al., Curr. Top. Microbiol. Immunol., 240:59 [1999]), protoplast electroporation (e.g., Bates, Methods Mol. Biol., 111:359 [1999]), viral infection (e.g., Porta and Lomonossoff, Mo. Biotechnol. 5:209 [1996]), microinjection, and liposome injection. Standard molecular biology techniques are common in the art (See e.g., Sambrook, J. et al., *Molecular Cloning: A Laboratory Manual*, $2^{nd}$ ed., Cold Spring Harbor Laboratory Press, New York [1989]). For example, in one embodiment of the present invention tobacco or *arabidopsis* is transformed with a gene encoding UCP using *Agrobacterium*.

A wide variety of promoters have been isolated from plants, which are functional not only in the cellular source of the promoter, but also in numerous other plant species. There are also other promoters (e.g., viral and Ti-plasmid) which can be used. For example, these promoters include promoters from the Ti-plasmid, such as the octopine synthase promoter, the nopaline synthase promoter, the mannopine synthase promoter, promoters from other open reading frames in the T-DNA, such as ORF7, etc. Promoters isolated from plant viruses include the 35S promoter from cauliflower mosaic virus (CaMV). Promoters that have been isolated and reported for use in plants include ribulose-1,3-biphosphate carboxylase small subunit promoter, phaseolin promoter, etc.

Using any of the above gene transfer techniques, an expression vector harboring the gene of interest is transformed into the desired plant sample to achieve temporary or prolonged expression of the gene. Any suitable expression system may be used, so long as it is capable of undergoing transformation and expressing of the gene of interest in the host. In one embodiment of the present invention, a pET vector (Novagen, Madison, Wis.), or a pBI vector (Clontech, Palo Alto, Calif.) is used as the expression vector. In some embodiments an expression vector further encoding a green fluorescent protein (GFP) is used to allow simple selection of transfected cells and to monitor expression levels. Examples of such vectors include Clontech's "Living Colors Vectors" pEYFP and pEYFP-C1. The EYFP gene is codon optimized for high expression in plant cells.

Site-specific recombinases catalyze recombination reactions between two nucleotide sequences referred to as recombination sites. If such recombination sites are integrated into genomic DNA, depending on the orientation of these sites relative to each other, i.e., direct or inverted, the intervening genomic DNA sequence can be either inverted or excised by certain site-specific recombinases. If the recombination sites are on two different chromosomes, some of the recombinases can catalyze the exchange of chromosomal fragments. Thus, site-specific recombination reactions have the potential to have substantial practical applications in genetic engineering.

Techniques for targeted insertion and the deletion of DNA from transgenic plant chromosomes are useful in the methods of the invention. The Cre-lox recombination system may be used for the controlled excision of DNA fragments from the nuclear and chloroplast genomes, and for the targeted insertion of DNA into specific sites in the nuclear genome. The Cre-lox system provides an efficient and precise tool for plant genetic manipulations. The FLP/FRT system from the *Saccharomyces cerevisiae*, can recognize and recombine FRT sites located in a plasmid molecule in several plants.

Once the cells accumulate or store fatty acid the fatty acids may be collected from the oil producing cell. Many methods for collecting the fatty acids from cells are known in the art. For instance, the fatty acids may be collected directly in the form of fatty acids or may be processed into other materials such as biofuels prior or after partial or total separation from the other components of the cell.

The fatty acids produced in the methods of the invention may be further processed to produce a biofuel. Thus, the biofuels can be generated from oil producing cells that have been treated with an herbicide that promotes oil secretion and optionally a compound that alters metabolism in a manner that allows accumulation of fatty acids. Such modified oil producing cells contain high amounts of vegetable oil, i.e. corn, palm, soybean, algae, jatropha, or pongamia pinnata. A biofuel as used herein is a solid, liquid or gaseous fuel obtained from a biological material and can be any fuel, fuel additive, aromatic, and/or aliphatic compound derived from a biomass starting material such as algae, corn, switchgrass etc. Biofuels include for instance, syngas and biodiesel.

The fatty acids produced by the metabolic disruption of plants or fungus can be processed in many different ways to produce biofuels. For instance, the fatty acids may be heated, to reduce the viscosity. The reduced viscosity fatty acids can be burned directly in a diesel engine. Alternatively they may be chemically processed to produce fuels such as biodiesel.

Syngas (synthesis gas) is a fuel that is a mixture of carbon monoxide and hydrogen that is produced by partial combustion of biomass. The combustion includes an amount of oxygen that is not sufficient to convert the biomass completely to carbon dioxide and water. The biomass may be dried, and/or pyrolyzed prior to the partial combustion. The syngas may be in some instances more efficient than direct combustion of the original biofuel because more of the energy contained in the fuel is extracted. Syngas may be burned directly in internal combustion engines or turbines.

Biodiesel is produced from fats using a process known as transesterification and is a liquid similar in composition to fossil/mineral diesel. Its chemical name is fatty acid methyl (or ethyl) ester. Oils are mixed with sodium hydroxide and methanol (or ethanol) and the chemical reaction produces biodiesel and glycerol. One part glycerol is produced for every 10 parts biodiesel.

One advantage of the invention is that the oil is secreted by the cells and can be harvested directly without manipulation of the cells. However, it is possible in some embodiments of the invention to harvest the secreted oil as well as the oil that remains within the cell by manipulation of the cells, i.e. algae using known methods in the art.

A variety of methods for processing of the oil loaded cells of the invention into biodiesel are known in the art and any such known method may be used in the practice of the instant invention. For example, the algae may be harvested, separated from the liquid medium, lysed and the oil content separated. The oil stored inside the plant cell or algae or fungus can be recovered in several relatively simple ways, including solvents, heat, and/or pressure. Other methods involve depolymerizing, such as biologically breaking the walls of the algal cell and/or oil vesicles, if present, to release the oil from the oil-producing algae.

In one example, fatty acids can be extracted in an oil extraction bioreactor which may be connected to the algae growth reservoirs. Within the oil extraction bioreactor the cell walls and algal oil vesicles of the oil-producing algae can be biologically ruptured to yield an algal oil and algal residue. An active agents can be used for releasing algae energy stores, i.e. enzymes such as cellulase or glycoproteinase, structured enzyme arrays or system such as a cellulosome, a viral agent such as a virus or viral lysate, or a combination thereof. A cellulase is an enzyme that breaks down cellulose, especially in the wall structures, and a cellulosome is an array or sequence of enzymes or cellulases which is more effective and faster than a single enzyme or cellulase. In both cases, the enzymes break down the cell wall and/or oil vesicles and release oil or starch from the cell. Cellulases used for this purpose may be derived from fungi, bacteria, or yeast. Non-limiting examples of each include cellulase produced by fungus *Trichoderma reesei* and many genetic variations of this fungus, cellulase produced by bacteria genus *Cellulomonas*, and cellulase produced by yeast genus *Trichosporon*. A glycoproteinase provides the same function as a cellulase, but is more effective on the cell walls of microalgae, many of which have a structure more dependent on glycoproteins than cellulose.

In addition, a large number of viruses exist which invade and rupture algae cells, and can thereby release the contents of the cell. Specific examples of such viruses include the *chlorella* virus PBCV-1 (Paramecium *Bursaria Chlorella* Virus) which is specific to certain *Chlorella* algae, and cyanophages such as SM-1, P-60, and AS-1 specific to the blue-green algae *Synechococcus*.

Mechanical crushing, for example, an expeller or press, a hexane or butane solvent recovery step, supercritical fluid extraction, can also be useful in extracting the oil from oil vesicles of the oil-producing algae. Alternatively, mechanical approaches can be used in combination with biological agents in order to improve reaction rates and/or separation of materials.

Once the oil has been obtained, i.e., either from the culture following secretion or from the processed cells, it can be recovered or purified by sedimentation or centrifugation. The recovered oil can be collected and directed for further processing.

The oil produced in these methods may be rich in hydrocarbons and/or triglycerides. A triglyceride consists of three fatty acid chains, one attached to each of the three carbon atoms in a glycerol backbone. This form of oil can be burned directly or converted into a biodiesel fuel. Such oils may be converted into biodiesel using well-known methods. One process for converting the triglyceride to biodiesel is transesterification, and includes reacting the triglyceride with alcohol or other acyl acceptor to produce free fatty acid esters and glycerol. The free fatty acids are in the form of fatty acid alkyl esters (FAAE). Standard transesterification processes involve an alkaline catalyzed transesterification reaction between the triglyceride and an alcohol, typically methanol. The fatty acids of the triglyceride are transferred to methanol, producing alkyl esters (biodiesel) and releasing glycerol. The glycerol is removed and may be used for other purposes.

In contrast to batch reaction methods (e.g., J. Am. Oil Soc. 61:343, 1984), the Connemann process (see, e.g., U.S. Pat. No. 5,354,878, incorporated herein by reference) utilizes continuous flow of the reaction mixture through reactor columns, in which the flow rate is lower than the sinking rate of glycerine. This results in the continuous separation of glycerine from the biodiesel. The reaction mixture may be processed through further reactor columns to complete the transesterification process. Residual methanol, glycerine, free fatty acids and catalyst may be removed by aqueous extraction. The Connemann process is well-established for production of biodiesel from plant sources such as rapeseed oil. Any method known in the art for producing biodiesel from triglyceride containing oils may be utilized, for example as disclosed in U.S. Pat. Nos. 4,695,411; 5,338,471; 5,730,029; 6,538,146; 6,960,672, each incorporated herein by reference. Alternative methods that do not involve transesterification may also be used. For example, by pyrolysis, gasification, or thermochemical liquefaction (see, e.g., Dote, 1994, Fuel 73:12; Ginzburg, 1993, Renewable Energy 3:249-52; Benemann and Oswald, 1996, DOE/PC/93204-T5).

Transesterification often uses a simple alcohol, typically methanol derived from petroleum. When methanol is used the resultant biodiesel is called fatty acid methyl ester (FAME) and most biodiesel sold today, especially in Europe, is FAME. However, ethanol can also be used as the alcohol in transesterification, in which case the biodiesel is fatty acid ethyl ester (FAEE). In the U.S., the two types are usually not distinguished, and are collectively known as fatty acid alkyl esters (FAAE), which as a generic term can apply regardless of the acyl acceptor used. Direct hydrogenation can also be utilized to convert at least a portion of the fatty acids to a biodiesel.

The fatty acids may also be converted to biodiesel by direct hydrogenation. In this process, the products are alkane chains, propane, and water. The glycerol backbone is hydrogenated to propane, so there is substantially no glycerol produced as a byproduct. Furthermore, no alcohol or transesterification catalysts are needed. All of the biomass can be used as feed for the oil-producing algae with none needed for fermentation to produce alcohol for transesterification. The resulting alkanes are pure hydrocarbons, with no oxygen, so the biodiesel produced in this way has a slightly higher energy content than the alkyl esters, degrades more slowly, does not attract water, and has other desirable chemical properties.

Optionally, the algae may be used as a source of waste disposal while also producing enhanced quantities of fatty acids. For instance, U.S. Pat. No. 7,208,530 describes such methods. Additionally, GreenFuel Technologies Corporation uses algae to absorb smokestacks flue gases and produce biofuels such as biodiesel, biogas and a dry fuel comparable to coal.

Each of the compositions of the invention may optionally be associated with a delivery system or vector or may be delivered alone. In its broadest sense, a "vector" is any vehicle capable of facilitating: (1) delivery of a composition to a target cell or (2) uptake of a composition by a target cell, if uptake is important. In general, the vectors useful in the invention are divided into two classes: colloidal dispersion systems and biological vectors.

As used herein, a "colloidal dispersion system" refers to a natural or synthetic molecule, other than those derived from bacteriological or viral sources, capable of delivering to and releasing the active agent to the plant cell. Colloidal dispersion systems include macromolecular complexes, beads, and lipid-based systems including oil-in-water emulsions, micelles, mixed micelles, and liposomes. A preferred colloidal system of the invention is a liposome. Liposomes are artificial membrane vessels. It has been shown that large unilamellar vessels (LUV), which range in size from 0.2-4.0µ can encapsulate large macromolecules within the aqueous interior and these macromolecules can be delivered to cells in a biologically active form (Fraley, et al., *Trends Biochem. Sci.*, 6:77 (1981)).

Lipid formulations for transfection are commercially available from QIAGEN, for example as EFFECTENE™ (a non-liposomal lipid with a special DNA condensing enhancer) and SUPER-FECT™ (a novel acting dendrimeric technology) as well as Gibco BRL, for example, as LIPO-FECTIN™ and LIPOFECTACE™, which are formed of cationic lipids such as N-[1-(2, 3 dioleyloxy)-propyl]-N,N,N-trimethylammonium chloride (DOTMA) and dimethyl dioctadecylammonium bromide (DDAB). Methods for making liposomes are well known in the art and have been described in many publications. Liposomes were described in a review article by Gregoriadis, G., *Trends in Biotechnology* 3:235-241 (1985), which is hereby incorporated by reference.

Other exemplary compositions that can be used to facilitate uptake by a target cell of the compositions of the invention include calcium phosphate and other chemical mediators of intracellular transport, microinjection compositions, electroporation and homologous recombination compositions (e.g., for integrating a composition of the invention into a preselected location within the target cell chromosome).

As used herein the term "transgenic" when used in reference to a plant or fruit (i.e., a "transgenic plant" or "transgenic fruit") refers to a plant or fruit that contains at least one heterologous gene in one or more of its cells.

As used herein, the term "sample" is used in its broadest sense. In one sense it can refer to a plant cell or tissue. In another sense, it is meant to include a specimen or culture obtained from any source, as well as biological and environmental samples. Biological samples may be obtained from plants or animals and encompass fluids, solids, tissues, and gases. Environmental samples include environmental material such as surface matter, soil, water, and industrial samples. These examples are not to be construed as limiting the sample types applicable to the present invention.

The words "transformants" or "transformed cells" include the primary transformed cell and cultures derived from that cell without regard to the number of transfers. All progeny may not be precisely identical in DNA content, due to deliberate or inadvertent mutations. Mutant progeny that have the same functionality as screened for in the originally transformed cell are included in the definition of transformants.

As used herein, the term "selectable marker" refers to the use of a gene that encodes an enzymatic or other detectable activity (e.g., luminescence, fluorescence, or radioactivity) that confers the ability to grow in medium lacking what would otherwise be an essential nutrient. A selectable marker may also confer resistance to an antibiotic or drug upon the cell in which the selectable marker is expressed. Selectable markers may be "dominant"; a dominant selectable marker encodes an enzymatic or other activity (e.g., luminescence, fluorescence, or radioactivity) that can be detected in any cell line.

The term "transfection" as used herein refers to the introduction of foreign DNA into cells. Transfection may be accomplished by a variety of means known to the art including calcium phosphate-DNA co-precipitation, DEAE-dextran-mediated transfection, polybrene-mediated transfection, glass beads, electroporation, microinjection, liposome fusion, lipofection, protoplast fusion, viral infection, biolistics (i.e., particle bombardment) and the like.

The following examples are provided to illustrate specific instances of the practice of the present invention and are not to be construed as limiting the present invention to these examples. As will be apparent to one of ordinary skill in the art, the present invention will find application in a variety of compositions and methods.

EXAMPLES

The experiments described herein examined the utility of Metabolic Disruption Technology (MDT) and herbicides for enhanced secretion of oil. The exemplary MDT compound used in the studies is sodium oxamate and the herbicide is glyburide. Initially increases in Nile Red fluorescence within *P. Parvum*, *Chlorella* sp. and *Schizochytrium* sp. following exposure to a range of sodium oxamate concentrations was observed. Additionally, an increase in Nile Red fluorescence was observed in the growth medium environment following treatment with glyburide, suggesting that lipids were secreted by the algal cells. These data, included in FIGS. 10-12, use the lipid-binding fluorescent compound Nile Red to track enhanced lipid accumulation in Schizochytrium and Chlorella in response to sodium oxamate. Another study was designed to further characterize the effects of 1) a single concentration of sodium oxamate (0.3 mM) on lipid accumulation within Chlorella sp. cells and 2) a single concentration of glyburide (0.05 mM) on the accumulation of lipids in the extracellular environment. The study was designed to track and quantify hydrocarbons (HC), β-carotene (BC), triacyglycerol (TG), and chlorophyll (Chl). This experimental study is described in FIGS. 1-9 and effectively demonstrated that the methods are effective on a larger scale.

Example 1

Methods:

Sodium Oxamate Dosing: Sodium oxamate was added to three of the four cultures (see FIG. 1). A 1 L sample was collected at time 0, 24 and 48 hours for each culture (a total of 4 samples per time point). The algal cells were pelleted and oils extracted at each time point. Quantitative oil profiles of extracted lipids were generated by TLC and HPLC. The studies demonstrated that 0.3 mM dose of sodium oxamate at scale, including quantitative and compositional analysis of accumulated oil. The experimental approach for sodium oxamate treatment is shown in FIG. 1.

Figure 2:
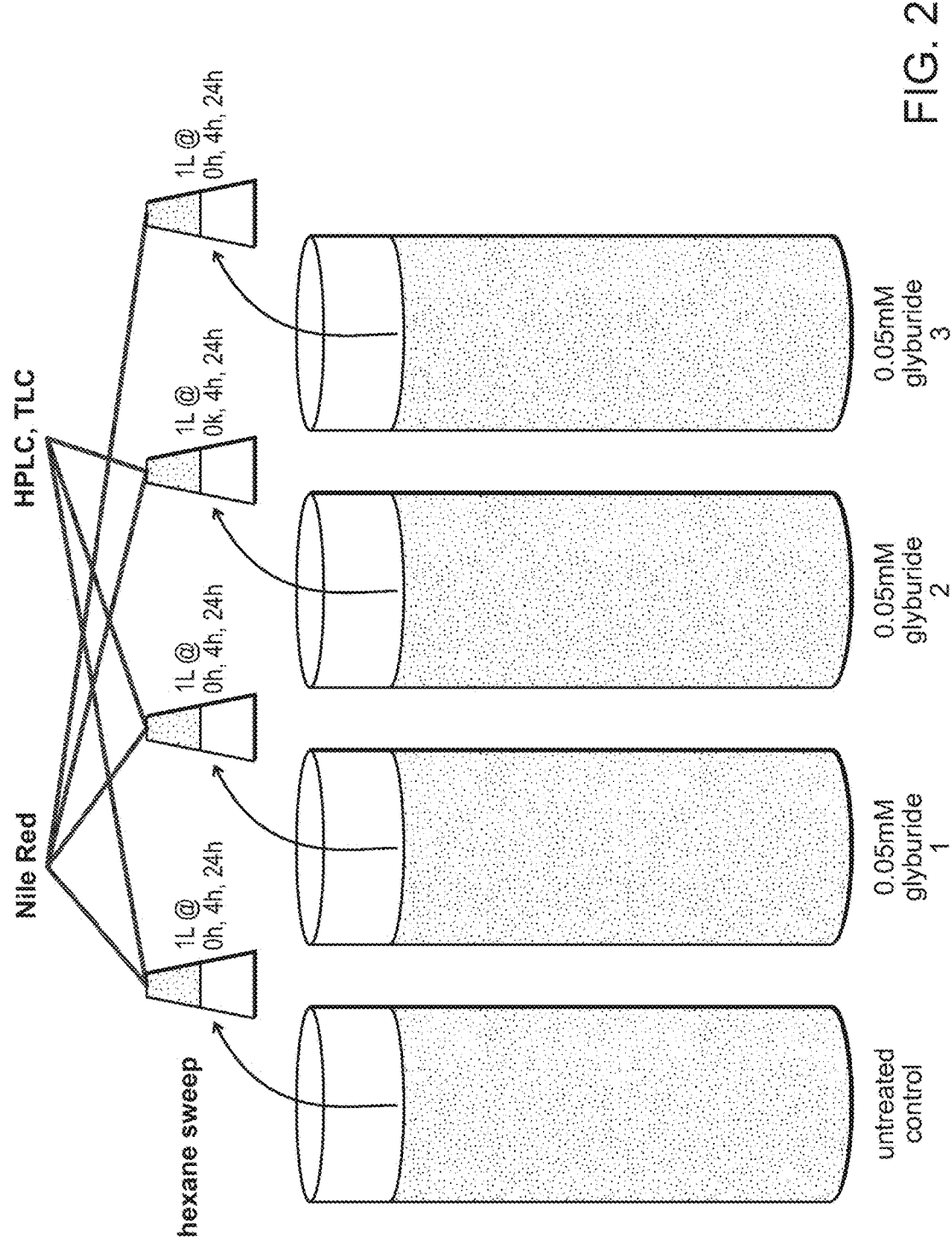
FIG. 2 is a schematic diagram of an experimental approach for glyburide treatment of algae.

Glyburide Dosing: After 48 hours, the sodium oxamate time course was complete. The same cultures were used to conduct a scaled trial of the glyburide compound (experimental approach is shown in FIG. 2). A 1 L sample of each culture was collected and treated to recover oil outside the cells (if any) at t=0. The three cultures that had previously been treated with sodium oxamate were subsequently treated with 0.05 mM glyburide. Extracellular lipids in 1 L aliquots of the cultures were collected at 4 hours and 24 hours after the addition of glyburide by hexane sweep; dry cell weights were also calculated on separate aliquots of the culture. Oils recovered were analyzed via TLC and HPLC. Demonstration of 0.05 mM dose of glyburide at scale, including quantitative and compositional analysis of oil secreted (see FIG. 2).

Algal growth: KAS603, a Chlorella sp. was scaled in F/2 growth medium to ~300 L in a vertical air lift bioreactor under 12/12 artificial illumination. Growth of the culture was monitored for density, chlorophyll accumulation, and for the presence of invasive species. Growth kinetics were typical and observation of invasive species was limited (sparse bacteria) and typical. The algae were grown under nutrient rich and light limiting conditions. These conditions do not typically lead to high triglyceride (TAG) accumulation.

Dry Weight Analysis: 10 ml of control and treated culture samples were pelleted via centrifugation at 3000 rpm for 5 minutes. The pellet was washed 1× with dH2O to remove salts. Following a second centrifugation step, the pellet was transferred to a pre-weighed aluminum dish and dried to a constant weight at 26.5° C.

Cellular Growth/Density: Cellular growth and density can be characterized by the concentration of chlorophyll a in a sample. Chlorophyll a absorbs light at 435 nm and 680 nm, which can be accurately measured spectrophotometrically. Prior to the dry weight analysis, 10 ml samples were analyzed for absorbance at 435 nm and 680 nm. Based on the established chlorophyll a standard curve, chlorophyll a was calculated and reported as "mg chlorophyll a".

Total lipid extraction: 1 L samples were pelleted via centrifugation at 3000 rpm for 5 min. The pellets were resuspended in 10 ml of methanol and incubated at 65° C. for 1 h. The methanol was replaced with chloroform and incubated at 50° C. for 10 min. The chloroform was replaced with hexane and incubated at 50° C. for an additional 10 min. The extracts were pooled and distilled. The weights of the dried extracts were recorded prior to resuspension in 100 µl chloroform for TLC analysis, or in 2:1 chloroform: methanol (v/v) to a final concentration of ~10 mg/mL and loaded for HPLC analysis (Surveyor LC Pump and Autosampler Plus, Thermo Finnegan). A splitter (Analytical Scientific Instruments) was employed to divide the sample 1:20 between a quadrapole MS (Thermo Finnegan MSQ Plus) and an ELSD (Sedere Sedex 75), respectively.

Lipid Analyses: TLC—Dried extracts were resuspended in 100 µl of CHCl3. 2.5 µl of each sample was spotted onto silica gel matrix TLC plates (Sigma #2599) and resolved with hexane:diethyl ether:acetic acid (80:20:1). Carotenoids such as β-carotene were visible as yellow bands on the plate, while chlorophyll and chlorophyll breakdown products were visible as green or green/gray bands, respectively. Lipids other than carotenoids and chlorophyll were visualized with iodine vapors. The extracted samples were compared to commercially available lipid standards consisting of 1 µg/µl each of glyceryl trioleate (TAG), 1,3-Diolein (1,3 DAG), 1,2-dioleoyl-rac-glycerol (1,2 DAG), monoolein (MAG), and oleic acid (FFA).

Recovery and Measurement of Extracellular Lipids: Cells that were exposed to the secretion compound glyburide were swept briefly with hexane at room temperature. 50 ml of hexane was added to 1 L samples from each study group, then mixed thoroughly, but gently, by inversion. The cells were re-centrifuged and the hexane layer containing the recovered lipids was transferred to a pre-weighed vial. The hexane was evaporated and the dried lipids were re-weighed. The dried lipids were subsequently analyzed by TLC or HPLC/MS as described.

Results

Figure 3:
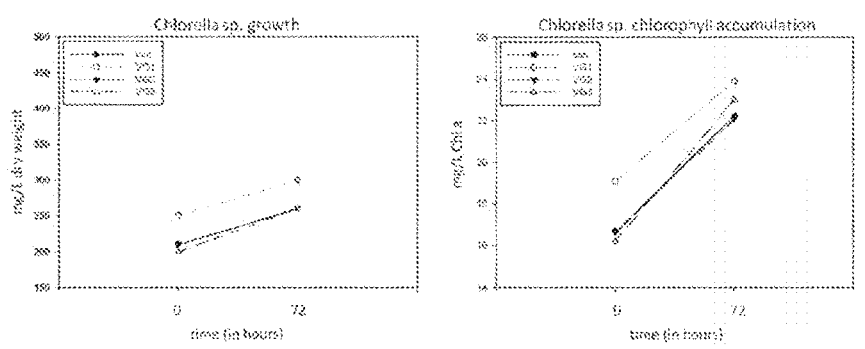
FIG. 3 is a bar graph depicting culture densities and chlorophyll counts obtained during treatment of algae with sodium oxamate or glyburide. The growth progress of the four 80 L cultures during the treatment period is shown. There is no evidence that compound treatment slowed growth.

FIG. 3 shows the growth progress of the four 80 L cultures during the treatment period. The cell density (by dry weight) was approximately 200 mg/L for each culture and increased by about 25% during the study (left panel). In addition, the chlorophyll a content of each culture increased during the study, independent of the compound treatments. The cultures were actively growing during the study, and there is no evidence that compound treatment slowed growth.

The extraction process used to collect the total lipid fraction following sodium oxamate treatment was thorough and complete. The de-lipidified biomass remaining after the extraction was compared to an unextracted sample. Bleaching of the samples indicated complete extraction.

The total oil extracts from the pellets were submitted for quantitative HPLC analysis to investigate changes in lipid profile and accumulation. The gross quantities of oil recovered from each pellet were recorded, as were representative dry weights. Quantitative HPLC analyses, using standard curves of expected species, including TAG, β-carotene, chlorophyll and hydrocarbon were conducted to determine amounts of expected species. Quantities of known oil species detected in the extracts are reported in FIG. 5. The analyses show that increases in chlorophyll and total lipids were detected in treated versus untreated groups. Significant TAG accumulation was not found in any of the oil extracts regardless of compound treatment. The quantity of "other" lipid species trended higher in the oxamate treated cultures. As shown in FIGS. 8A and B, there were also increases in uncharacterized polar lipids following oxamate treatment. The total lipid extracts of the pellets were also characterized by TLC.

In the glyburide treatment study, externalized lipids were recovered at T=0, T=4 hours and T=24 hours after the addition of 0.05 mM glyburide. The absolute mass of oil recovered for each time point was determined by weight. During the recovery of lipid, the raw hexane extractions were visibly colored in the treated groups, but not in the control group, indicating that oil was recovered from outside the cells.

The weights of oil recovered by hexane sweep are shown in Table 1. Interestingly, there were no immediate increases in external oil at 4 hours. By 24 hours after glyburide exposure, significantly larger quantities of oil were recovered. The study was discontinued at 24 hours post glyburide. Other data (not shown here) demonstrated that assessed oil after 48 hours, where a visible sheen was observed. The quantities of oil are reported as grams from 1 L of culture media.

TABLE 1

Weights of oil recovered from outside cells following glyburide treatment (in g; NT—no treatment).

|      | T = 0  | T = 4  | T = 24 |
|------|--------|--------|--------|
| GLB1 | 0.0003 | 0.0002 | 0.0016 |
| GLB2 | 0.0002 | 0.0004 | 0.0014 |
| GLB3 | 0.0003 | 0.0004 | 0.0013 |
| NT   | 0.0002 | 0.0002 | 0.0002 |

The oils recovered were also submitted for normalized HPLC characterization. The oil fraction did not consist primarily of TAG as expected (see FIG. 7 below and FIG. 8).

FIG. 8 depicts a representative chromatograms from untreated controls, oxamate-, and glyburide-treated samples from the same *Chlorella* culture. A) untreated control at time=0, B) sodium oxamate-treated (0.3 mM) at 48 h, C) extracellular lipid profile from the untreated control (same culture as shown for the glyburide traces), D) extracellular lipid profile from the glyburide-treated (0.05 mM) at 24 h. Neutral lipids eluted from the column within 24 min, while polar lipids elute with retention times >24 min. Following 0.05 mM glyburide treatment for 24 hrs, neither β-carotene nor chlorophyll were detected outside the cells. This is as expected, as the oil recovery method does not extract intracellular constituents, it only collects extracellular oils. An increase in external hydrocarbon however, was observed in the glyburide treated samples (compare 8C and 8D). In addition, the difference in total oil recovered was substantial, in treated groups versus untreated, but the increased mass could not be conclusively assigned to a peak by HPLC (compare 8C and 8D).

Based on the lack of beta-carotene and chlorophyll in the recovered oils, which are present inside, but not outside the cells, we conclude the species was external to the cells. The existing HPLC methods cannot prospectively quantitate or identify unknown oils, as column binding affinities of uncharacterized oil are unknown. Elucidation and new method development would be required to quantify this species by HPLC. To investigate further, we conducted TLC.

Figure 9:
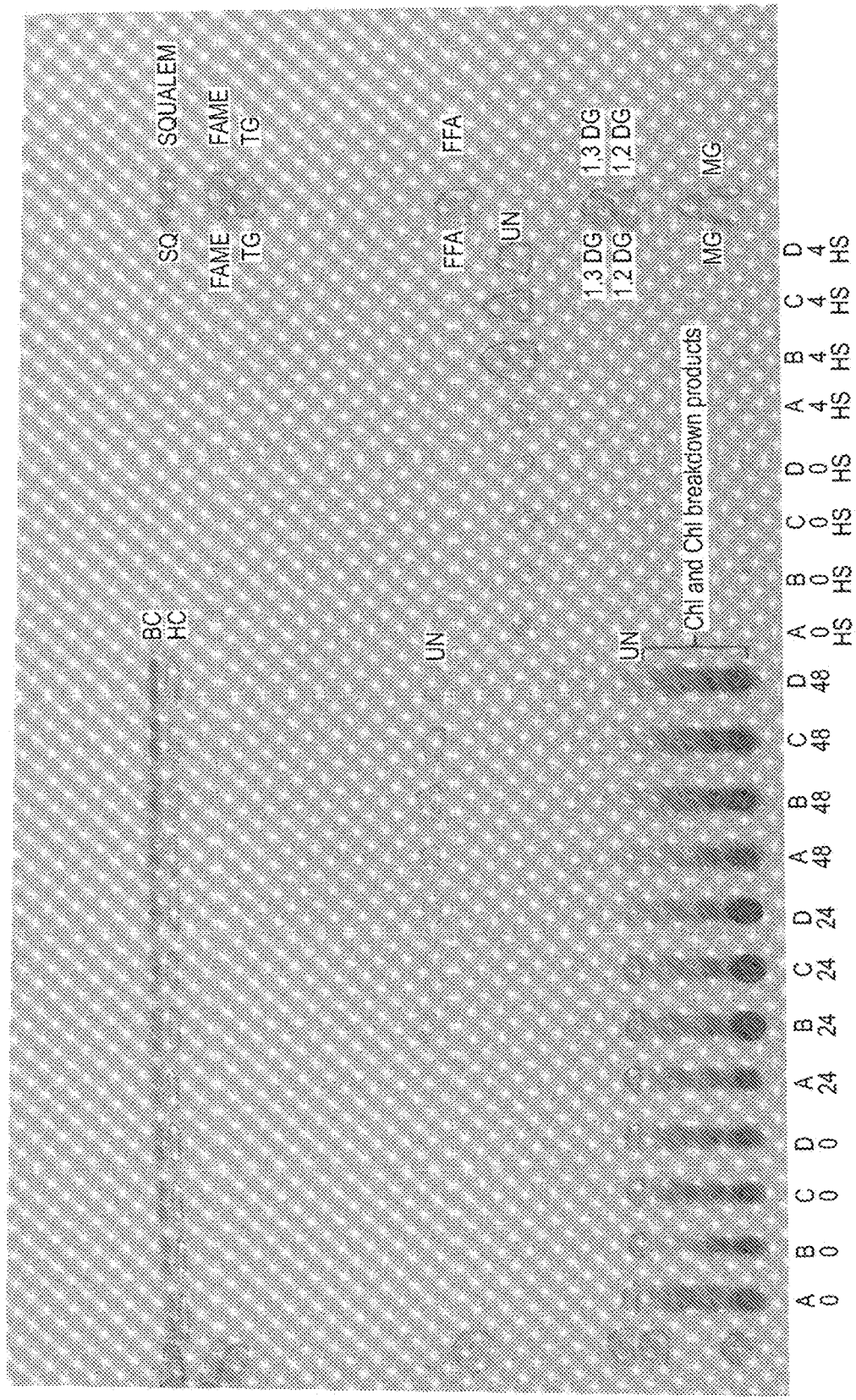
FIG. 9 shows a TLC plate analysis performed to qualitatively track lipid accumulation over the duration of the entire study. The bottom of the plate depicted the samples labeled as follows: control (A), and oxamate-treated (B-D), cultures (left side) and the glyburide-treated samples (right side). Lipid standards bracket the study samples (SQ—squalene, FAME—fatty acid methyl ester, TG—triacylglycerol, FFA—free fatty acid, 1,3DG—1,3 diacylglycerol, 1,2DG—1,2 diacylglycerol, MG—monoglycerides, Chl—chlorophyll, UN—undefined lipid).

TLC was performed to qualitatively track lipid accumulation over the duration of the entire study, and relevant samples were subjected to TLC together to allow direct comparisons (FIG. 9). The TLC method used is highly complementary to HPLC because it separates only non-polar oils and also allows the detection of species of unknown composition. One drawback of TLC is that it is significantly less sensitive than HPLC. Typically only abundant oil species are easily detected.

FIG. 9 is a picture of a TLC plate of the control (A), and oxamate-treated (B-D), cultures (left side) and the glyburide-treated samples (right side). Lipid standards bracket the study samples (SQ—squalene, FAME—fatty acid methyl ester, TG—triacylglycerol, FFA—free fatty acid, 1,3DG—1,3 diacylglycerol, 1,2DG—1,2 diacylglycerol, MG—monoglycerides, Chl—chlorophyll, UN—undefined lipid).

TLC generally separates species by polarity, with the least polar species at the top of the plate (hydrocarbon) and the more polar species (chlorophyll, green) at the bottom. The samples on the left side are total lipid extracts from the oxamate study. Hydrocarbon (HC) and β-carotene (BC) concentrations remained consistent throughout the oxamate treatment phase and, as shown in the HPLC traces, minor amounts of TAG and DAG were present. Small quantities of undefined lipids (UN) were detected in total extracts by TLC but these lipids did not differ between treated and untreated groups.

The TLC analysis of the extracellular lipids recovered during the glyburide study revealed unexpected results. One or more lipid species with intermediate polarity with respect to free fatty acids (FFA) and 1,3-diacyglycerol (1,3DG), were detected. The quantity of this lipid species was significantly increased in the glyburide treated groups. Interestingly, this same species was not detected in the total extracts of the samples during the oxamate phase.

Example 2

Methods: Growth and Maintenance of *Schizochytrium*

The media used for maintaining *Schizochytrium* is 790 BY+ medium. It is prepared as follows. 1.0 g of yeast extract, 1.0 g of Peptone and 5.0 g of D+ Glucose were added to an autoclaveable glass bottle with 1 L of sterile sea water. The mixture was autoclaved at 121 C.° for 15 minutes.

*Schizochytrium* were removed from liquid nitrogen storage tank. 100 mL of 790 BY+ medium was added to a 250 mL Erlenmeyer flask. The cells were thawed in at 37 C.° water bath until completely liquid and then transferred to the 250 mL Erlenmeyer flask. A foam stopper was placed in the flask opening and the flask was placed on a shaker stirrer. Once every 7 days 2 mL of the *Schizochytrium* were transferred into a new 250 mL Erlenmeyer flask containing 100 mL of 790 BY+ medium.

For flow cytometric analysis, the desired number of flow tubes were labeled (4 per treatment group). For microscopy, the desired number of microscope slides were labeled (2 per treatment). A culture of *Schizochytrium* was obtained. Count *Schizochytrium* and resuspend to obtain a concentration of $1 \times 10^6$ cells per 100 µL of PBS. $5 \times 10^6$ cells per treatment group were used for flow cytometry and $2 \times 10^6$ were used for microscopy.

Flow Cytometry

*Schizochytrium* were harvested, counted, and resuspended at $10^6$ cells/100 µl of PBS containing 2.5% fetal calf serum in preparation for flow cytometric analysis. Lysosensor dyes were used to detect fatty acids in glyoxosomes or oil droplets. Mitochondrial membrane potential was assessed using Mitotracker Red (CM-H$_2$XROS, BD Pharmingen). The cells were resuspended in PBS containing 2.5% fetal calf serum containing a final concentration of 0.5 micromolar Mitotracker dye. The cells were incubated at 37° for 20 minutes, washed twice in PBS containing 2.5% fetal calf serum and analyzed flow cytometrically. Data were acquired on a Coulter Excel flow cytometer (Coulter, Hialeah, Fla.) and analyzed with FloJo software. The Coulter Excel flow cytometer has a single excitation wavelength (488 nm) and band filters for PE (575 nm), FITC (525 nm) and Red613 (613 nm) that was used to analyze the stained cells. Each sample population was classified for cell size (forward scatter) and complexity (side scatter), gated on a population of interest and evaluated using 30,000 cells.

Cell Counting

Cells were harvested and resuspended in 1 mL of seawater medium or Phosphate Buffered Saline (PBS) supplemented with 2.5% FBS, and 5 µL of the cell suspension. Live cells were counted using a hemocytometer and the following calculation was used to determine cell number: Average # of Cells×Dilution×10$^4$.

Results

Figure 10:
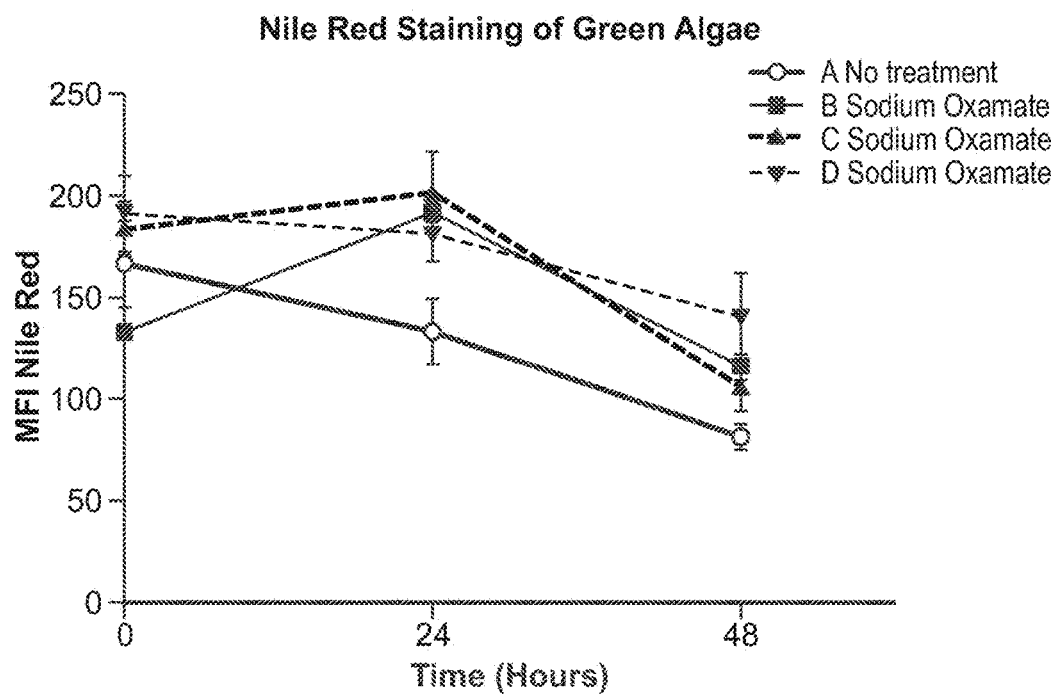
FIG. 10 is a bar graph depicting Nile red staining of green algae either treated with sodium oxamate or no treatment.
Figure 11:
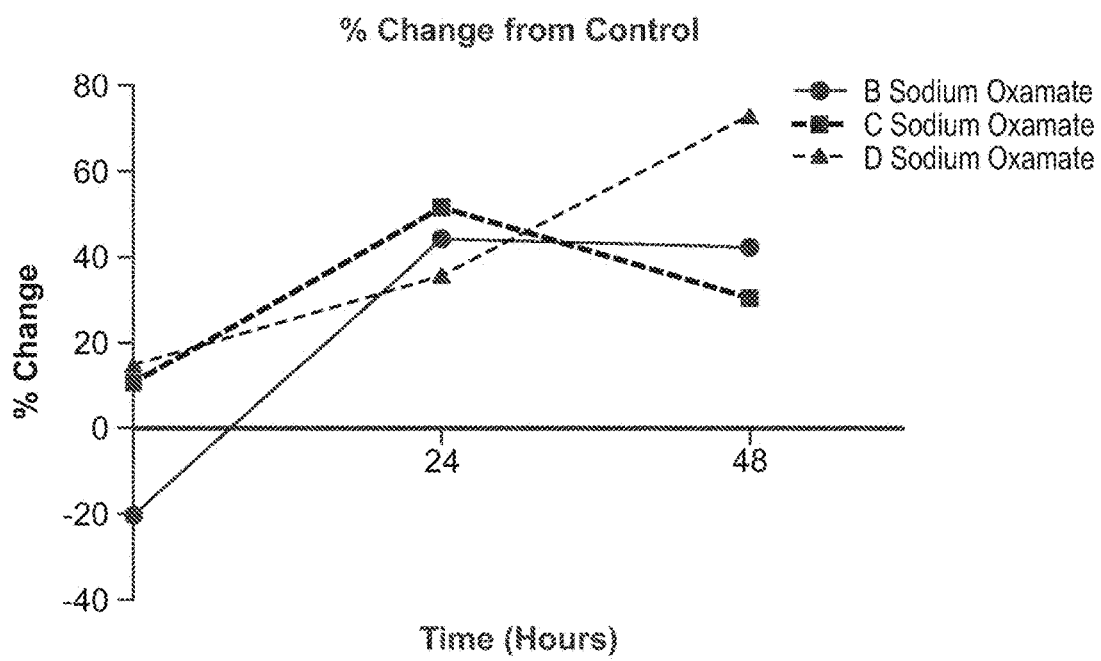
FIG. 11 is a bar graph depicting the percent change in lipid production with time in response to treatment of algae with sodium oxamate.
Figure 12:
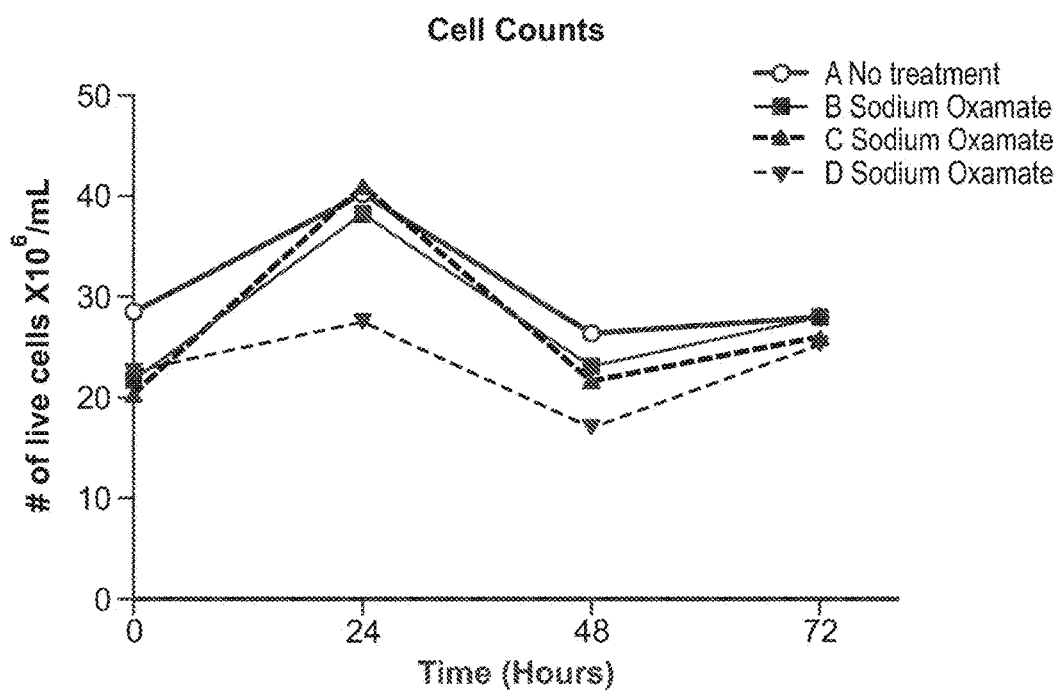
FIG. 12 is a bar graph depicting the number of live algae cells over time in treated (sodium oxamate) versus untreated cells.

Algae treated with sodium oxamate were examined for changes in fatty acid accumulation. FIG. 10 is a bar graph depicting Nile red staining of green algae either treated with sodium oxamate or no treatment. FIG. 11 is a bar graph depicting the percent change in lipid production with time in response to treatment of algae with sodium oxamate. The cells were also examined to determine the effects of the sodium oxamate treatment on viability. FIG. 12 is a bar graph depicting the number of live algae cells over time in treated (sodium oxamate) versus untreated cells.

Example 3: Enhanced Production of Oils in *P. Parvum*

A control culture of *P. Parvum* was grown and split into two 500 mL cultures. Glyburide was added to one of the cultures and the culture was shaken for 24 h.

After the cultures sat for an hour an oily sheen that was much more prevalent on the surface of the glyburide treated culture than the control culture was observed. Interestingly, the sheen appeared with glyburide treatment, even in the absence of oxamate.

A 1 L *P. parvum* culture (~2 million cells/mL) treated with oxamate was split into two subcultures of 400 mL each. Glyburide dissolved in DMSO was added to one subculture. The other subculture received the DMSO carrier (control) that the glyburide had been dissolved in. The two cultures were incubated on the shaker for 24 h and subsequently off the shaker for ~2 h.

The glyburide treated culture appeared to have a number of swirls on the surface, apparently made by the oil secreted from the cells. The control culture, in contrast, had very few swirls.

Figure 4:
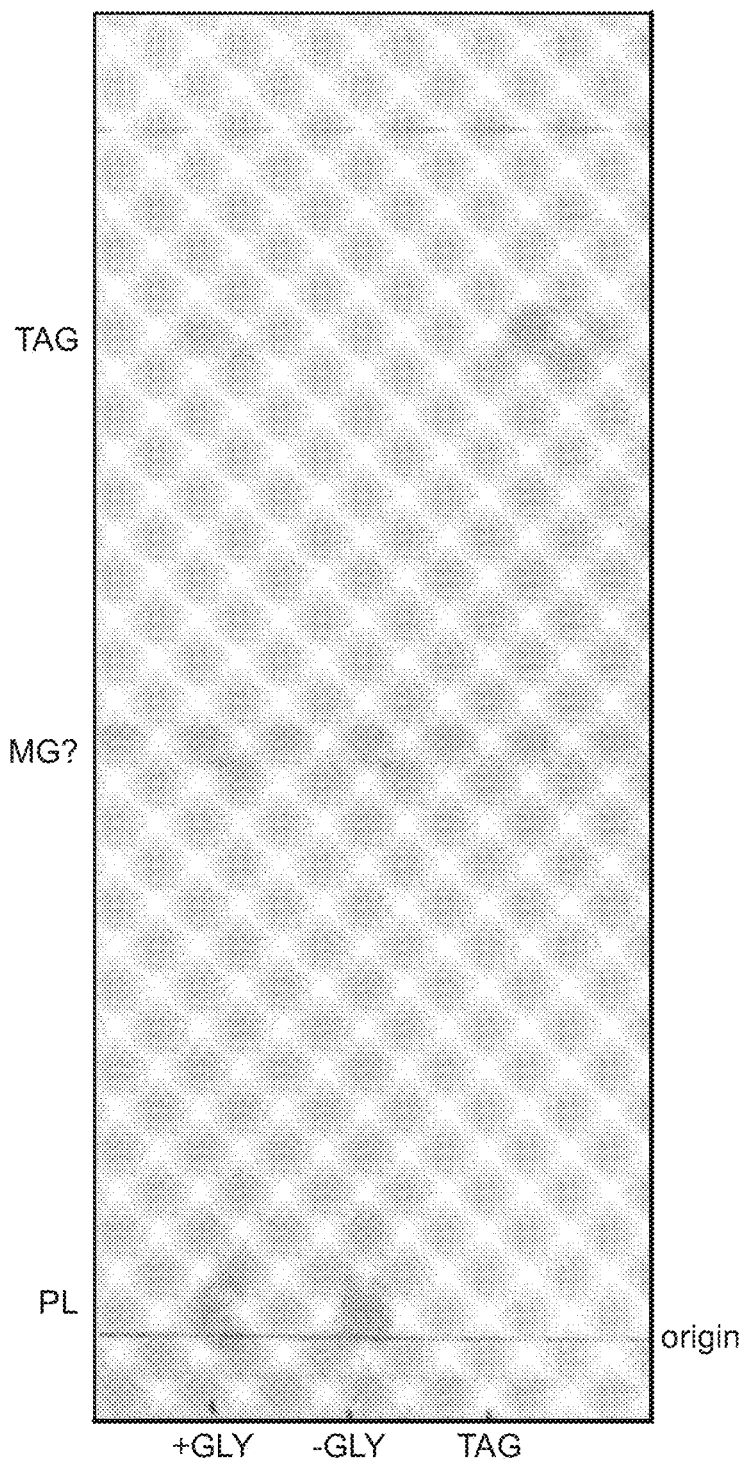
FIG. 4 is a chromatogram depicting the effects of glyburide/oxamate treatment on lipid production and secretion in *P. Parvum*.
Figure 5A:
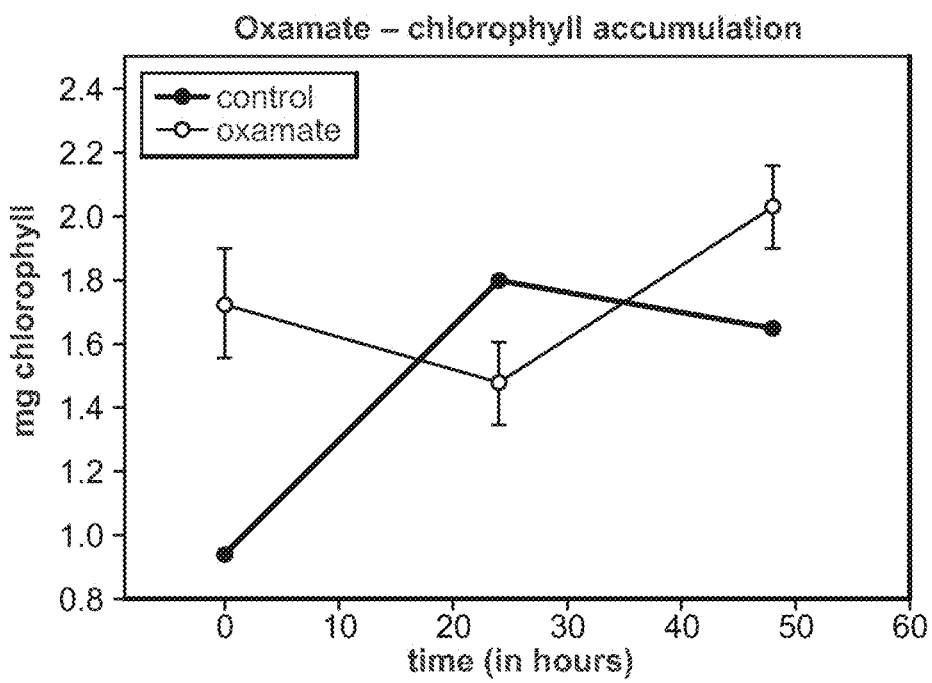
FIG. 5 is a series of bar graphs depicting the lipids detected in total extracts from the sodium oxamate treatment schematically shown in FIG. 1. The gross quantities of oil recovered from each pellet were recorded, as were representative dry weights. Quantitative HPLC analyses, using standard curves of expected species, including TAG (5D), B-carotene (5B), chlorophyll (5A) and hydrocarbon (5C) were conducted to determine amounts of expected species. Quantities of an unknown oil species detected in the extracts is shown in FIG. 5E.
Figure 5B:
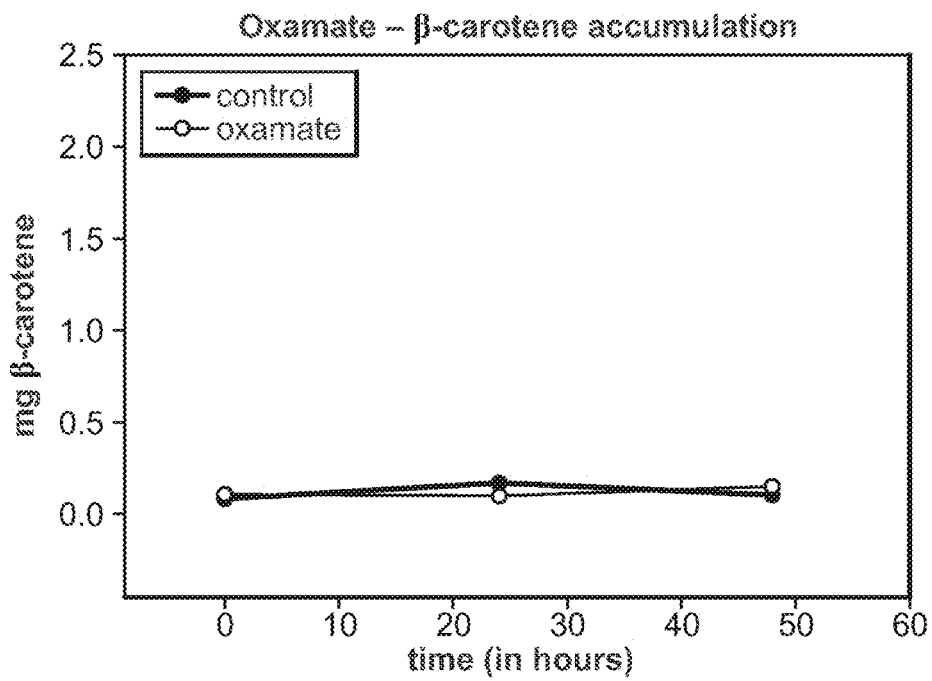
Figure 5C:
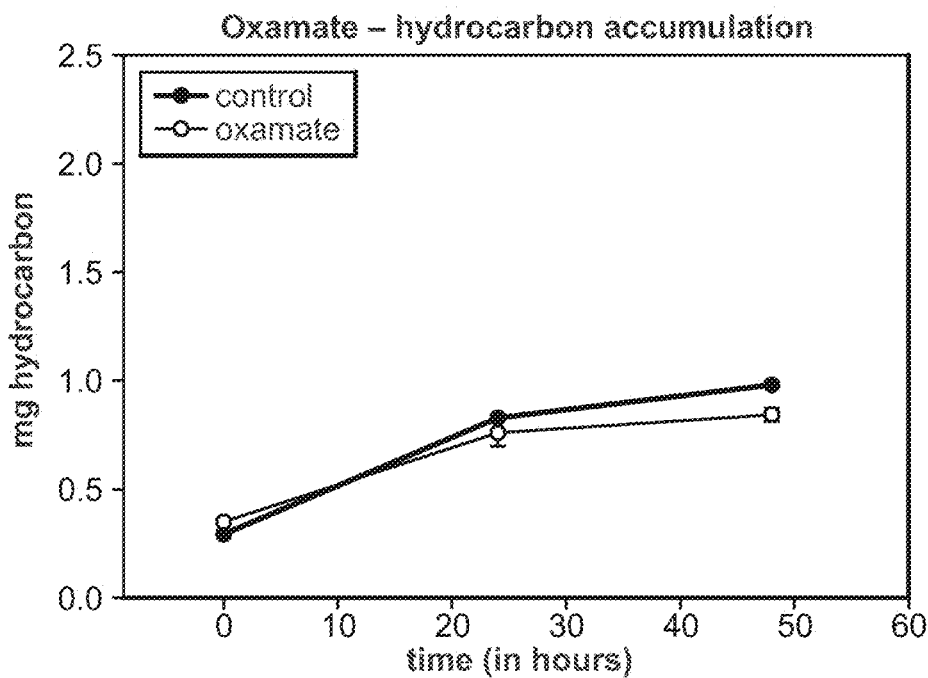
Figure 5D:
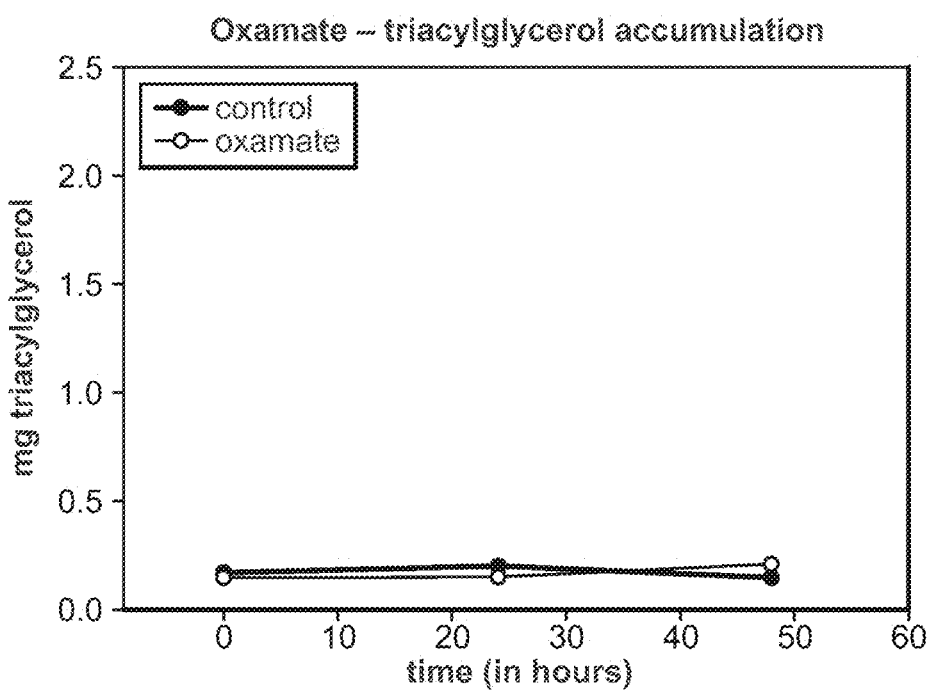
Figure 5E:
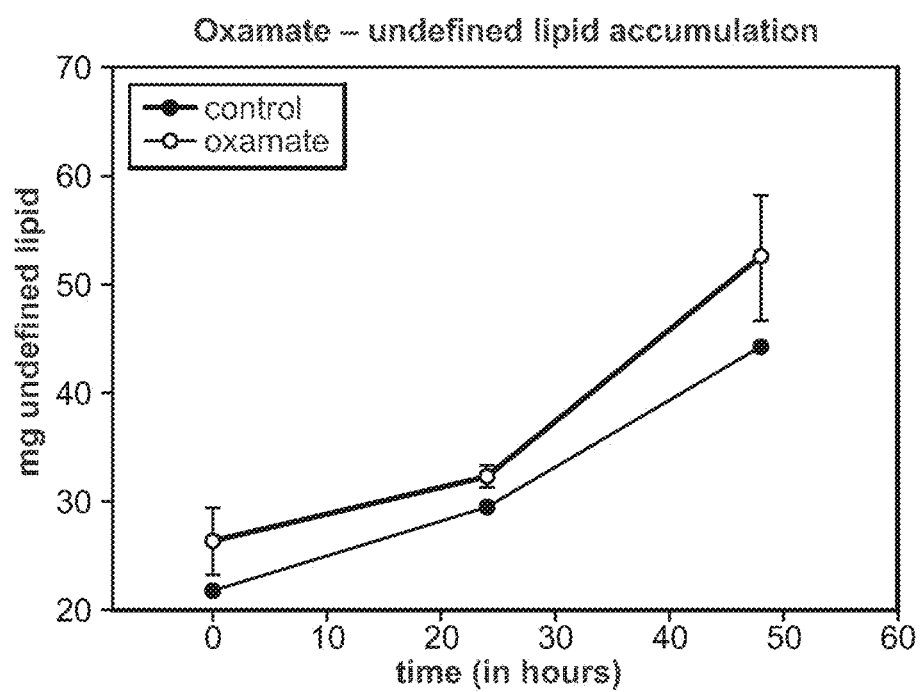
Figure 6:
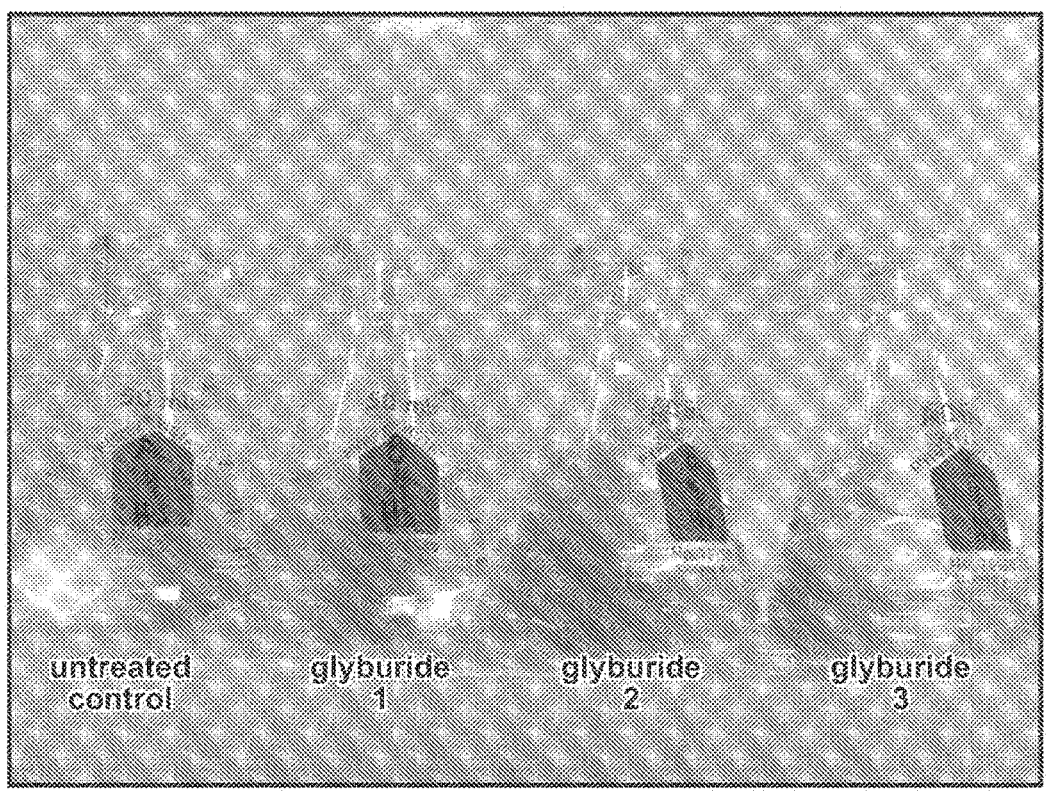
FIG. 6 is a photograph of clear flasks holding liquid samples from either untreated control or the three glyburide treated algae cultures (treated as depicted in FIG. 2). In the glyburide treated samples, externalized lipids were recovered at T=0, T=4 hours and T=24 hours after the addition of 0.05 mM glyburide. The absolute mass of oil recovered for each time point was determined by weight. During the recovery of lipid, the raw hexane extractions were visibly colored in the treated groups, but not in the control group, indicating that oil was recovered from outside the cells.
Figure 7A:
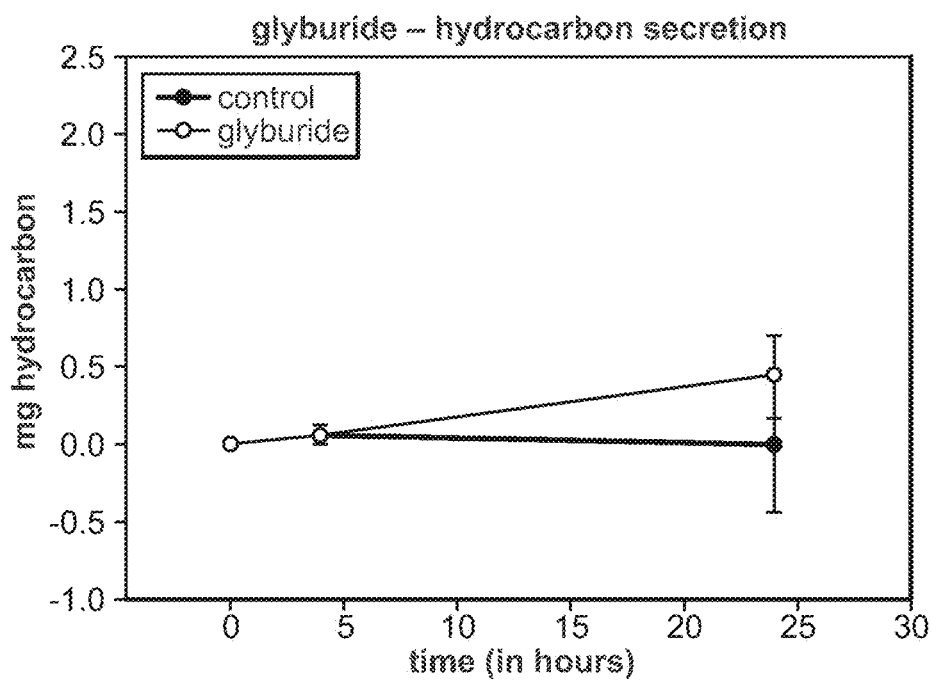
FIG. 7 is a bar graph depicting the results of an HPLC analysis of oil isolated from outside cells following glyburide exposure.
Figure 7B:
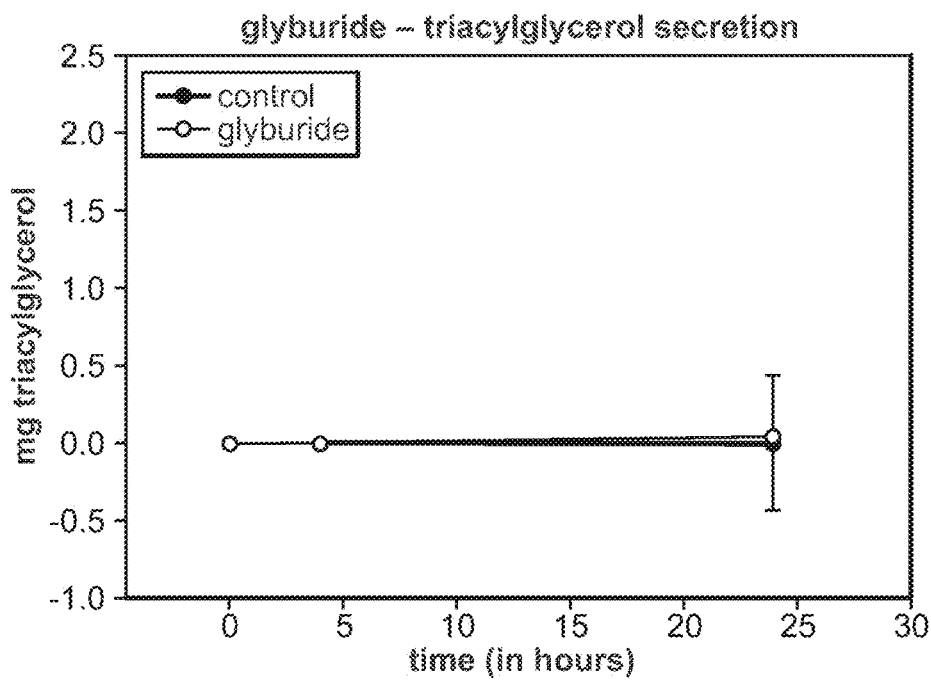
Figure 7C:
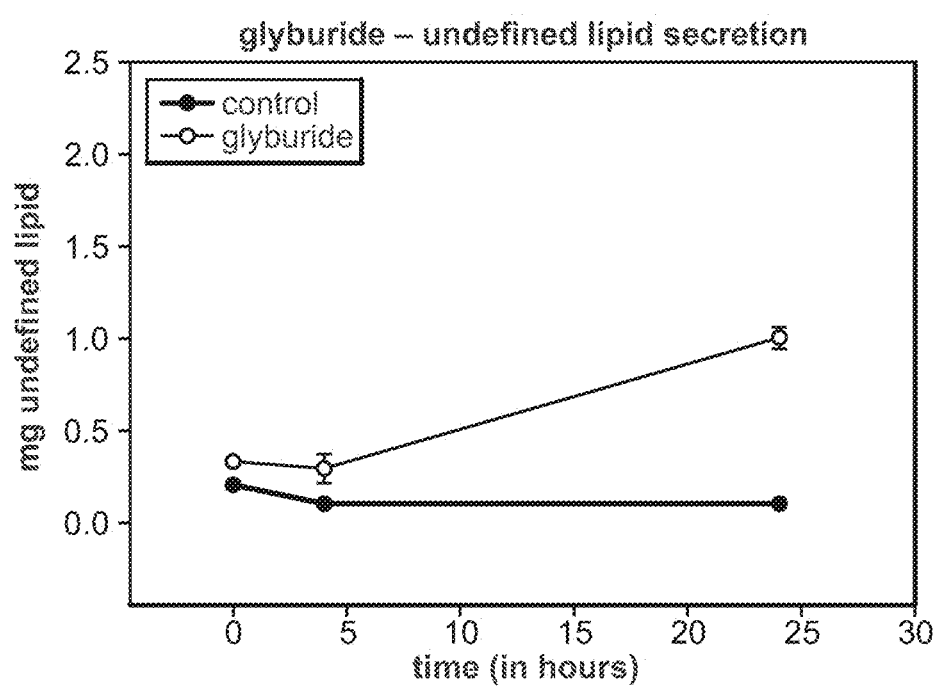

The cells were then pelleted and a 200 mL sample of the culture supernatant was removed from each culture. Each of the removed samples was briefly extracted with nonpolar solvent. The organic extracts were then dried down and the remainder was resuspended in an equal volume of solvent. An equal volume of each (as well as pure TAG as a standard) was loaded on a TLC plate. A chromatogram was developed and stained with iodine vapors. The results are shown in FIG. 4. The glyburide/oxamate-treated subculture did indeed increase the production and/or secretion of lipid, specifically triacylglyceride (TAG), particularly when compared to the control, which was lacking in TAG. Both subcultures had similar amounts of phospholipids (PL). This is likely due to the presence of dead cell membranes in the supernatant extract. Both test samples also had either some monoglycerides (MG) or more likely, the pigment fucoxanthin.

The results in FIG. 4, confirm that *P. parvum* not only produces the economically-valuable TAG, but cells will secrete it into the growth medium after being treated with glyburide. Other than phospholipids, there are nearly no other species of lipids evident in the supernatants.

Example 4: Growth Curves of Oxamate Treated Algae

Small-scale (15-0 mL) *P. Parvum* cultures were grown and treated with oxamate. Four (A-D in FIG. 13) of the small scale cultures were treated with oxamate stock in growth medium, added every three days, corresponding to the points on the curve. Two (E-F in FIG. 13) of the cultures had only growth medium added.

Figure 13:
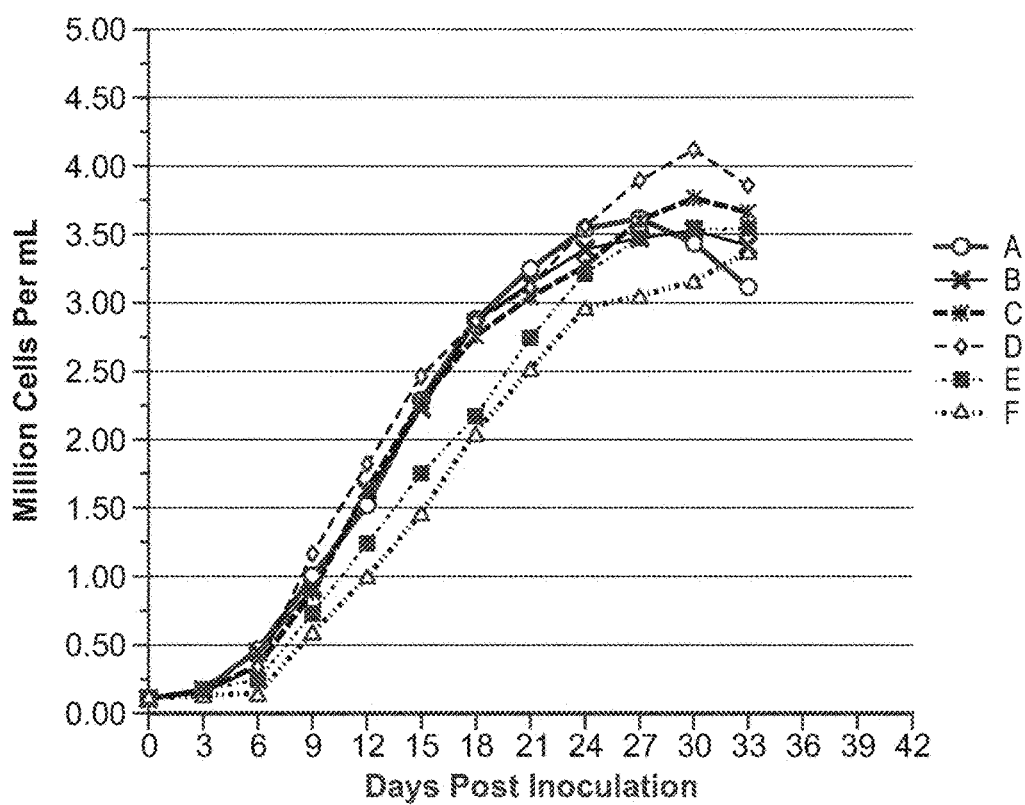
FIG. 13 is a growth curve graph depicting the results of a spike-in oxamate experiment on algae cultures.

The results of the growth analysis are shown in FIG. 13. The oxamate-containing cultures typically achieved higher cell concentrations than did the controls, and they began to decline sooner than the controls. The results appear to be comparable to those achieved with oxamate treated cultures where the oxamate is added only at the initiation of cultivation (data not shown, from a separate experiment).

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

I claim:

1. A method, comprising contacting an oil producing cell from a plant, fungus or algae with an herbicide comprising a K<sub>ATP</sub> channel receptor inhibitor, wherein the inhibitor comprises sulfonylurea in an amount of at least 0.05 mM to promote secretion of recoverable oil from the cell in excess of 1 mg/L accumulated after at least 24 hours of said contacting, and collecting said recoverable oil.

2. The method of claim 1, wherein the method is a method for preparing a biofuel and further comprising processing the oil to produce a biofuel.

3. The method of claim 1, wherein the sulfonylurea is selected from the group consisting of Chlorpropamide, glimepiride, glyburide, glipizide, Tolazamide, and Tolbutamide.

4. The method of claim 1, wherein the sulfonylurea is glyburide.

5. The method of claim 1, wherein the oil is processed to produce biofuel using a pyrolysis process.

6. The method of claim 1, wherein the oil producing cell is an algae.

7. The method of claim 6, wherein the algae is a *schizochytrium*.

8. The method of claim 1, wherein the biofuel is syngas.

9. The method of claim 8, wherein the syngas is processed by a FischerTropsch reaction to produce a biodiesel.

10. The method of claim 1, further comprising contacting the oil producing cell with an inhibitor of fatty acid metabolism.

11. The method of claim 10, wherein, the inhibitor of fatty acid metabolism is an inhibitor of fatty acid oxidation, a fatty acid transporter inhibitor, a reductase inhibitor, or an isomerase inhibitor.

12. The method of claim 11 wherein the reductase is 2,4-dienoyl CoA reductase.

* * * * *